(12) United States Patent
Bujnicki et al.

(10) Patent No.: US 9,353,358 B2
(45) Date of Patent: May 31, 2016

(54) SEQUENCE-SPECIFIC ENGINEERED RIBONUCLEASE H AND THE METHOD FOR DETERMINING THE SEQUENCE PREFERENCE OF DNA-RNA HYBRID BINDING PROTEINS

(71) Applicant: MIEDZYNARODOWY INSTYTUT BIOLOGII MOLEKULARNEJ I KOMORKOWEJ, Warsaw (PL)

(72) Inventors: Janusz Marek Bujnicki, Warsaw (PL); Agata Agnieszka Sulej, Warsaw (PL); Krzysztof Jerzy Skowronek, Hornowek (PL); Marcin Nowotny, Warsaw (PL)

(73) Assignee: MIEDZYNARODOWY INSTYTUT BIOLOGII MOLEKULARNEJ I KOMORKOWEJ, Warsaw (PL)

( * ) Notice: Subject to any disclaimer, the term of this patent is extended or adjusted under 35 U.S.C. 154(b) by 209 days.

(21) Appl. No.: 14/095,351

(22) Filed: Dec. 3, 2013

(65) Prior Publication Data
US 2014/0094385 A1    Apr. 3, 2014

Related U.S. Application Data

(63) Continuation-in-part of application No. PCT/PL2012/050019, filed on Jun. 7, 2012.

(60) Provisional application No. 61/494,494, filed on Jun. 8, 2011, provisional application No. 61/494,481, filed on Jun. 8, 2011.

(30) Foreign Application Priority Data

Jun. 8, 2011 (PL) ..................... P.395179
Jun. 8, 2011 (PL) ..................... P.395180

(51) Int. Cl.
*C12N 9/22* (2006.01)
*C07K 14/435* (2006.01)
*A61K 38/00* (2006.01)

(52) U.S. Cl.
CPC .............. *C12N 9/22* (2013.01); *C07K 14/435* (2013.01); *C12Y 301/26004* (2013.01)

(58) Field of Classification Search
None
See application file for complete search history.

(56) References Cited

U.S. PATENT DOCUMENTS

| 5,270,163 A | 12/1993 | Gold et al. |
| 2002/0160486 A1* | 10/2002 | Wu .......................... C12N 9/22 435/199 |

FOREIGN PATENT DOCUMENTS

| WO | WO 2007/014181 | 2/2007 |
| WO | WO 2009/126632 | 10/2009 |
| WO | WO 2010/076939 | 7/2010 |
| WO | WO 2011/022427 | 2/2011 |

OTHER PUBLICATIONS

Sundar Durai, et al., Zinc Finger Nucleases: Custom-Designer Molecular Scissors for Genome Engineering of Plant and Mammalian Cells, Nucleic Acids Research (2005) vol. 33, No. 18, p. 5978-5990.

Martin Nowotny, et al., Crystal Structures of RNase H Bound to an RNA/DNA Hybrid: Substrate Specificity and Metal-Dependent Catalysis; Cell (2005) vol. 121, p. 1005-1016.

Y. Shi, et al., Specific DNA-RNA Hybrid Binding by Zinc Finger Proteins, Science (1995) vol. 268, No. 5208, p. 282-284.

* cited by examiner

*Primary Examiner* — Manjunath Rao
*Assistant Examiner* — Samuel Liu
(74) *Attorney, Agent, or Firm* — Vedder Price P.C.; Thomas J. Kowalski; Deborah L. Lu

(57) ABSTRACT

The subject of the invention is the ribonuclease which cleaves RNA strand in DNA-RNA hybrids, wherein ribonuclease comprises fusion protein comprising catalytic domain of RNase HI (RNase HI) or derivative thereof with a zinc finger DNA-RNA hybrid binding domain, and wherein the zinc finger binding domain has the ability to bind to specific sequences in the DNA-RNA hybrid. The invention also relates to new methods for determination of the sequence preference of DNA-RNA hybrid binding protein(s) or its domain(s) and allows determining the sequence recognized by sequence specific binding protein in the DNA-RNA hybrid.

7 Claims, 9 Drawing Sheets

Fig. 1

| Primer name | Sequence | Number of SEQ ID No |
|---|---|---|
| Bhcatf | GACGCATATGGCAAAAGAGGAGATTATTTGGG | SEQ ID No:11 |
| Bhcatr | GTGGTACCTTTTCTCCCGTAATCGGC | SEQ ID No:12 |
| BhZf | GGTTCTGGTGACCCGGG | SEQ ID No:13 |
| Kmf | GGGATCGCAGTGGTGAGTAAC | SEQ ID No:14 |
| Kmr | CGGGAAAACAGCATTCCAGGTATTAG | SEQ ID No:15 |
| K81Ar | CCGTCTGGGAATCAGAATAGATC | SEQ ID No:16 |
| K81Af | CAATCGCATGGGTGAAGGATAAAAAG | SEQ ID No:17 |
| K89Er | CTGCTTTTTATCCTTCACCC | SEQ ID No:18 |
| K89Ef | CAATCGCATGGGTGAAGGATAAAAAG | SEQ ID No:19 |
| K123Ar | TAAGATGGGCGTTTCATAGGTATG | SEQ ID No:20 |
| K123Af | GCATGGCAGACCGATAAGTG | SEQ ID No:21 |
| del11f | GGCTCCGGCCAGCACGCGTGCCCGG | SEQ ID No:22 |
| del11r | AGAACCGCTCCCGTAATCGGCCTTAATTTCC | SEQ ID No:23 |
| del5f | CAAAAACAGCACGCGTGCCC | SEQ ID No:24 |
| del5r | CCCCCGTAATCGGCCTTAATTTCCC | SEQ ID No:25 |

Fig. 2

(A) RNA:

AGAACUAGUGGAUCAACCGGGCUGCAGGAAUUCGAUAUCAAGCUUAUCGAUAC
CGUGGCGGUUCUUCCCCAAGCC  (SEQ ID No:9)

(B) DNA:

GCTTGGGGAAGAACCGCCACGGTATCGATAAGCTTGATATCGAATTCCTGCAG
CCCGGTTGATCCACTAGTTCT (SEQ ID No:10)

Fig. 7

5'-AGAACUAGUGGAUCAACCGGGCUGCAGGAAUUCGAUAUCAAGCUUAUCGAUACCGUGGCGGUUCUUCCCCAAGCC-3'  SEQ ID NO:39
3'-TCTTGATCACCTAGTTGGCCCGACGTCCTTAAGCTATAGTTCGAATAGCTATGGCACCGCCAGAAGGGGTTCGG-5' SEQ ID NO:40

Fig. 8

5'-AGAACUAGUGGAUCAACCGGGCUGCAGGAAUUCGAUAUCAAGCUUAUCGAUACCGUGGCGGUUCUUCCCCAAGCC-3'  SEQ ID NO:39
3'-TCTTGATCACCTAGTTGGCCCGACGTCCTTAAGCTATAGTTCGAATAGCTATGGCACCGCCAGAAGGGGTTCGG-5' SEQ ID NO:40

Fig. 9

5'-AGAACUAGUGGAUCAACCGGGCUGCAGGAAUUCGAUAUCAAGCUUAUCGAUACCGUGGCGGUUCUUCCCCAAGCC-3'  SEQ ID NO:39
3'-TCTTGATCACCTAGTTGGCCCGACGTCCTTAAGCTATAGTTCGAATAGCTATGGCACCGCCAGAAGGGGTTCGG-5' SEQ ID NO:40

Template A:

GAGATCTAGACGGAACATGAAGGGGAAGAATTCTATGCTTAGTGAGATCTAGAGCC
CTATAGTGAGTCGTATTAAATT (SEQ ID No:26)

Template B:

GAGATCTAGACGGAACATGAAGCTCGAGCCTTCTATGCTTAGTGAGATCTAGAGCCC
TATAGTGAGTCGTATTAAATT (SEQ ID No:27)

Template 9N:

GAGATCTAGACGGAACATGTANNNNNNNNNTACTATGCTTAGTGAGATCTAGAGCC
CTATAGTGAGTCGTATTAAATT (SEQ ID No:28)

A)

LDNA: TCACTGGGGAAGAAGAATCCTC (SEQ ID No:29)
LRNA: GAGGAUUCUUCUUCCCCAGUGA (SEQ ID No:30)

B)

CDNA: TCACTGGTCGGTGGGAATCCTC (SEQ ID No:31)
CRNA: GAGGAUUCCCACCGACCAGUGA (SEQ ID No:32)

US 9,353,358 B2

SEQUENCE-SPECIFIC ENGINEERED RIBONUCLEASE H AND THE METHOD FOR DETERMINING THE SEQUENCE PREFERENCE OF DNA-RNA HYBRID BINDING PROTEINS

RELATED APPLICATIONS AND INCORPORATION BY REFERENCE

This application is a continuation-in-part application of international patent application Serial No. PCT/PL2012/050019 filed 7 Jun. 2012, which published as PCT Publication No. WO 2012/169916 on 13 Dec. 2012, which claims benefit of Polish patent application Serial Nos. P.395179 and P.395180 filed 8 Jun. 2011 and U.S. provisional patent application Ser. Nos. 61/494,494 and 61/494,481 filed 8 Jun. 2011.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Feb. 26, 2016, is named 46400_00_2003 SL.txt and is 22,111 bytes in size.

FIELD OF THE INVENTION

The invention concerns a sequence-specific ribonuclease H, which may comprise a fusion of an engineered ribonuclease HI (RNase HI) domain with a zinc finger domain. The present invention is applicable in genetics. The sequence-specific ribonuclease that acts on DNA-RNA hybrids is useful in any application, where cleavage of the RNA strand in a DNA-RNA hybrid can be performed, for example in in vitro manipulation of nucleic acids, particularly DNA-RNA hybrids with a specified sequence. In addition to in vitro use, enzymes that cleave DNA-RNA hybrids in a sequence specific manner may also find use in the therapy of certain RNA viruses infections (eg. oncogenic viruses, retroviruses, hepatitis B, influenza), which replicate by transiently forming a DNA strand on a RNA template or to cleave other DNA-RNA hybrids that are formed in vivo.

The invention also relates to a method for determination of the sequence preference of DNA-RNA hybrid binding protein(s) or its domain(s) and by this determining the sequence recognized by a DNA-RNA hybrid binding protein. The present invention in this scope is applicable in genetics. The method for determination of the sequence preference of DNA-RNA hybrid binding protein is applicable in determining the sequence preference of any protein or its domain that binds to specific sequences in the DNA-RNA hybrid and by this determining the sequence recognized by a DNA-RNA hybrid binding protein(s) or its domain. The method can be applied complementarily to any specificity engineering technique of such proteins. Sequence-specific DNA-RNA hybrid binding proteins can be used in the diagnosis of certain RNA viruses (e.g. oncogenic viruses, retroviruses, hepatitis B, influenza), which replicate by the transition to the creation of a DNA strand RNA template. Such domains can also be applied in protein engineering to obtain enzymes with new specificity such as DNA-RNA binding protein fusions with enzymatic domains, such as nuclease, RNA modification or DNA modification enzymes and others.

BACKGROUND OF THE INVENTION

Cleavage of nucleic acids in a specific location is frequently used in many genetic engineering techniques. There are many methods to fragment DNA molecules, including the widely used commercially available restriction enzymes. Not many RNA processing enzymes are known and most of them are characterized by a low sequential specificity or its total absence.

WO 2010076939 A1 relates to compositions and methods for carrying out targeted genetic recombination or mutation using the chimeric zinc finger nuclease. WO 03087341 A2 relates to the use of a zinc finger nuclease for the targeted editing of the human cystic fibrosis transmembrane conductance regulator gene, thereby providing a potential therapy for cystic fibrosis. WO 2009146179 A1 relates to the development of a highly efficient and easy-to-practice modular-assembly method using publicly available zinc fingers to make zinc finger nucleases that are able to modify the DNA sequences of several genomic sites in human cells. From descriptions WO2007014181A2 and WO2007014182A2 there are known fusions of many zinc finger domains and FokI nucleases that facilitate targeted genome editing. However, unlike in the former case, the fusion of native proteins alone, RNase HI and the zinc finger, does not lead to a sequence-specific enzyme.

The method for determination of the sequence preference of DNA-RNA hybrid binding protein(s) or its domain(s) and by this determining the sequence recognized by a DNA-RNA hybrid binding protein is a modification of the SELEX procedure. SELEX stands for systematic evolution of ligands by exponential enrichment. The principle of this method is based on iterative selection and enrichment of molecules from a large diverged library of nucleic acids sequences that exhibit a high affinity towards a ligand. The enrichment step is accomplished by binding of the nucleic acids to a ligand and removal of the unbound sequences.

WO 2010076939 A1 relates to the compositions and methods for carrying out the targeted genetic recombination or mutation using the chimeric zinc finger nuclease. WO 03087341 A2 relates to the use of a zinc finger nuclease for the targeted editing of the human cystic fibrosis transmembrane conductance regulator gene, thereby providing a potential therapy for cystic fibrosis. WO2009146179 A1 relates to the development of a highly efficient and easy-to-practice modular-assembly method using publicly available zinc fingers to make zinc finger nucleases that are able to modify the DNA sequences of several genomic sites in human cells.

Herskovitz M. A. et al., Mol Microbiol. 2000 December: 38(5):1027-33, "Endoribonuclease RNase III is essential in *Bacillus subtilis*" relates to growth of a strain in which Bs-RNase III (rncS) expression was dependent upon transcription of rncS from a temperature-sensitive plasmid and at the non-permissive temperature resulted in 90-95% cell death, and virtually all the cells that survived retained the rncS-expressing plasmid. Thus, authors concluded that rncS is essential in *B. subtilis*. Dasgupta S. et al., Mol Microbiol. 1998; 28 (3): 629-40, "Genetic uncoupling of the dsRNA-binding and RNA cleavage activities of the *Escherichia coli* endoribonuclease RNase III—the effect of dsRNA binding on gene expression." describes the phenotypes of bacteria carrying point mutations in mc, the gene encoding RNase III. Karen Shahbabian et al., The EMBO Journal (2009) 28, 3523-3533, "RNase Y, a novel endoribonuclease, initiates riboswitch turnover in *Bacillus subtilis*" describes an essential protein of earlier unknown function, YmdA, identified as a novel endoribonuclease (now called RNase Y) that was capable of preferential cleaving in vitro of the 5'-monophosphorylated yitJ riboswitch upstream of the SAM-binding aptamer domain.

US 2006057590 relates to the generation of a double stranded RNA molecule that substantially covers the whole transcribed region of a gene and cleaving this molecule using an RNA endonuclease to generate small RNA molecules, which are already or may be subsequently labeled. JP54059392 patent relates to a novel nuclease B-1 which attacks the single chain scission area of one of the DNA chains of a double-stranded deoxyribonucleic acid, and specifically splits the other DNA chain at its complementary area.

Citation or identification of any document in this application is not an admission that such document is available as prior art to the present invention.

DISCLOSURE OF INVENTION

None of WO 2010076939 A1, WO 03087341 A2 or WO 2009146179 A1 describes or suggests the use of the fusion of RNase HI or part thereof with a zinc finger, particular with ZfQQR nor in particular they disclose or suggest possibility for the targeted cleavage of DNA-RNA hybrids or any type of targeted cleavage of DNA-RNA hybrids by any protein.

This method was so far used for obtaining RNA and DNA aptamers that bind ligands with high specificity (Ellington, A. D., Szostak, J. W., 1990. Nature 346, 818-822; Huizenga D E, Szostak J W. 1995. Biochemistry 34(2):656-65"), for determining a sequence preference of a DNA or RNA binding protein (Blackwell T K & Weintraub H. 1990. Science 250: 1104-1110), but was never used for proteins that bind to DNA-RNA hybrids. The described oligonucleotide libraries used in known modifications of SELEX consisted of either single stranded oligonucleotides (RNA, ssDNA, modified RNA or modified ssDNA, PNA), or double stranded DNA (dsDNA), but none characterize the use of DNA-RNA hybrid library.

WO 2010076939 A1 and WO2009146179 A1 do not describe the use of SELEX method for determining the substrate preference of DNA-RNA hybrid binding proteins or use of zinc finger for binding of specific sequences in DNA-RNA hybrids or use of ZfQQR in particular for that purpose.

None of Herskovitz M. A. et al., Dasgupta S. et al. or Karen Shahbabian et al. mention or suggest the use of SELEX method for determining the substrate preference of DNA-RNA hybrid binding proteins or zinc fingers that bind to DNA-RNA hybrids or any method of obtaining DNA-RNA hybrids.

US 2006057590 and JP54059392 are silent of the use of SELEX method for determining the substrate preference of DNA-RNA hybrid binding proteins or use of zinc finger for binding of specific sequences in DNA-RNA hybrids or use of ZfQQR in particular for that purpose.

There is a need for a ribonuclease that cleaves the RNA strand of the DNA-RNA hybrids in a specific location. There is also a need for a new improved method of determining the substrate preference of DNA-RNA hybrid binding proteins or use of zinc finger for binding of specific sequences in DNA-RNA hybrids or in particular of use ZfQQR for that purpose.

An object of the presented invention is to overcome the indicated disadvantages and to deliver ribonuclease that cleaves the RNA strand of the DNA-RNA hybrids in a specific location. Therefore the object of the invention is to provide engineered enzyme based on combination of catalytic domain of RNase HI and the zinc finger domain that recognizes the sequence in DNA-RNA hybrids and to obtain a sequence-specific enzyme that cleaves only the RNA strand of the DNA-RNA hybrids.

The next object of the invention is to provide a new, improved method for obtaining a library of DNA-RNA hybrids with a random sequence and its use for determining the sequence preference of DNA-RNA hybrid binding protein, preferably sequence preference of DNA-RNA hybrid for binding by zinc finger, more preferably by ZfQQR. Such a method can be effectively used for screening DNA-RNA hybrid library. The next object of the invention is to provide a new and improved method of obtaining a library of DNA-RNA hybrids.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

All publications and references cited in the description and their references are entirely incorporated herein by reference.

BRIEF DESCRIPTION OF DRAWINGS

The following detailed description, given by way of example, but not intended to limit the invention solely to the specific embodiments described, may best be understood in conjunction with the accompanying drawings.

FIG. 1 shows the sequence of the primers of SEQ ID No:11-25 used in the preparation of the final DNA construct of a gene fusion rnhA gene with zinc finger ZfQQR and the preparation of substitutions in the RNase HI from *B. halodurans* gene sequence.

FIG. 2 is a sequence of DNA-RNA hybrid shown on SEQ ID No:9 (FIG. 2 (A)—RNA strand) and SEQ ID No:10 (FIG.

2 (B)—DNA strand) containing the binding site for zinc finger ZfQQR, which was used in digestion assays as specific substrate.

Figure 3:
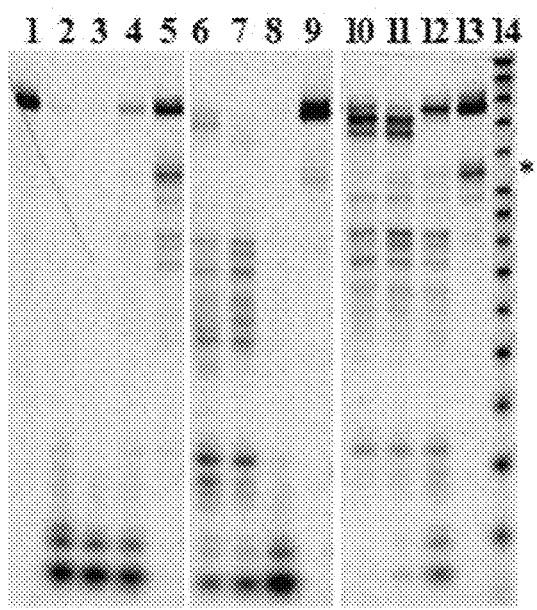

FIG. 3 shows the digestion products resulting from the cutting of the substrate DNA-RNA hybrid that contains the binding site for the zinc finger, and the dependence of the cleavage on the presence of magnesium and zinc ions. Digestion reaction shown in Lanes 1-14 were performed with 0.05 μM of the radioactively labeled substrate, 0.5 μM of non-labeled substrate, 25 mM Tris (pH 8.0), 100 mM KCl, 2 mM DTT, 30 min at 37° C. with presence or not of different enzyme and presence of 5 mM $MgCl_2$ and/or 20 μM $ZnSO_4$ as indicated below. Lane 1: uncleaved substrate, Lane 2: 12.5 nM of RNase HI from *B. halodurans*, 5 mM $MgCl_2$, 20 μM $ZnSO_4$, Lane 3: 625 nM of cat, 5 mM $MgCl_2$, 20 μM $ZnSO_4$, Lane 4: 5 nM cat-ZfQQR, 5 mM $MgCl_2$, 20 μM $ZnSO_4$, Lane 5: 25 nM catAEA-ZfQQR, 5 mM $MgCl_2$, 20 μM $ZnSO_4$, Lane 6: 12.5 nM of RNase HI from *B. halodurans*, 5 mM $MgCl_2$, Lane 7: 625 nM of cat, 5 mM $MgCl_2$, Lane 8: 5 nM cat-ZfQQR, 5 mM $MgCl_2$, Lane 9: 25 nM of catAEA-ZfQQR, 5 mM $MgCl_2$, Lane 10: 12.5 nM of RNase HI from *B. halodurans*, 20 μM $ZnSO_4$, Lane 11: 625 nM of cat, 20 μM $ZnSO_4$, Lane 12: 5 nM of cat-ZfQQR, 20 μM $ZnSO_4$, Lane 13: 25 nM of catAEA-ZfQQR, 20 μM $ZnSO_4$, Lane 14: Marker size 10-100 nucleotides single-stranded RNA radioactively labeled isotope phosphorus 33 (USB) where an asterisk (*) marked a unique cleavage site.

Figure 4:
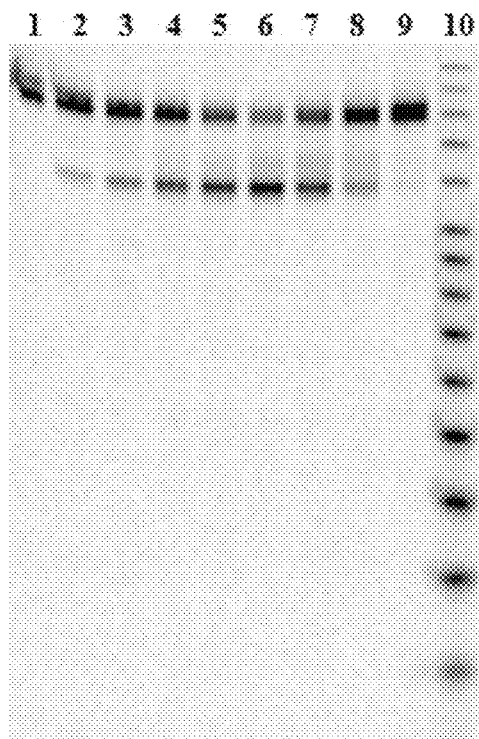

FIG. 4 shows the digestion products resulting from the cutting of the substrate DNA-RNA hybrid, which contains the binding site for the zinc finger, and the dependence of the cleavage by the variant GQ of the catAEA-ZfQQR on the presence of magnesium and zinc ions. Digestion reaction shown in Lanes 1-14 were performed with 50 nM of GQ variant, 0.05 μM of the radioactively labeled substrate, 0.5 μM of non-labeled substrate, 25 mM Tris (pH 8.0), 20 μM $ZnSO_4$, 100 mM KCl, 2 mM DTT, 30 min at 37° C. with various concentrations of $MgCl_2$ as indicated below. Lane 1: uncleaved substrate, Lane 2: 0.05 mM $MgCl_2$, Lane 3: 0.1 mM $MgCl_2$, Lane 4: 0.2 mM $MgCl_2$, Lane 5: 0.5 mM $MgCl_2$, Lane 6: 1 mM $MgCl_2$, Lane 7: 2 mM $MgCl_2$, Lane 8: 5 mM $MgCl_2$, Lane 9: 10 mM $MgCl_2$, Lane 10: Marker size 10-100 nucleotides single-stranded RNA radioactively labeled isotope phosphorus 33 (USB).

Figure 5:
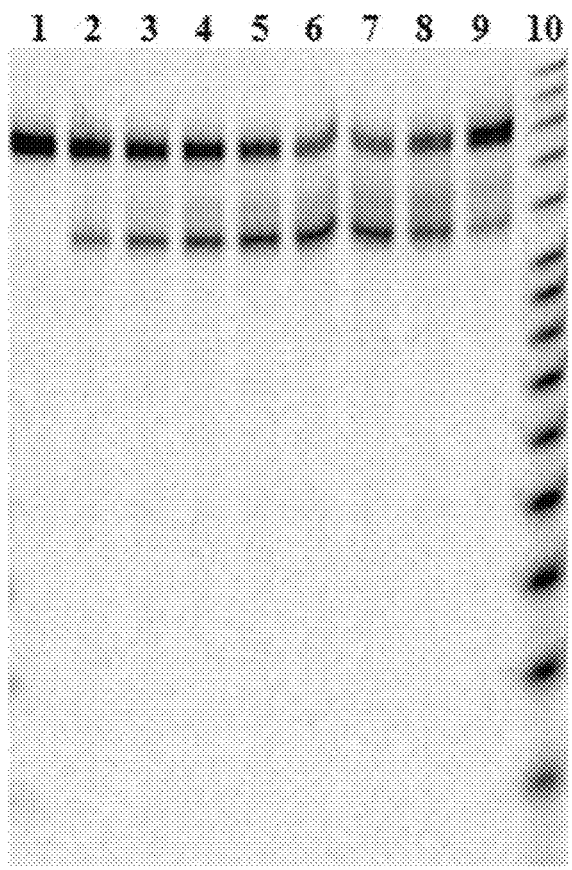

FIG. 5 shows the digestion products resulting from the cutting of the substrate DNA-RNA hybrid, which contains the binding site for the zinc finger, and the dependence of the cleavage by the variant glycine glycine lysine lysine glutamine (GGKKQ) of the catAEA-ZfQQR on the presence of magnesium and zinc ions. Digestion reaction shown in Lanes 1-14 were performed with 50 nM GGKKQ variant, 0.05 μM of the radioactively labeled substrate, 0.5 μM of non-labeled substrate, 25 mM Tris (pH 8.0), 20 μM $ZnSO_4$, 100 mM KCl, 2 mM DTT, 30 min at 37° C. with various concentrations of $MgCl_2$ as indicated below: Lane 1: uncleaved substrate, Lane 2: 0.05 mM $MgCl_2$, Lane 3: 0.1 mM $MgCl_2$, Lane 4: 0.2 mM $MgCl_2$, Lane 5: 0.5 mM $MgCl_2$, Lane 6: 1 mM $MgCl_2$, Lane 7: 2 mM $MgCl_2$, Lane 8: 5 mM $MgCl_2$, Lane 9: 10 mM $MgCl_2$, Lane 10: Marker size 10-100 nucleotides single-stranded RNA radioactively labeled isotope phosphorus 33 (USB).

Figure 6:
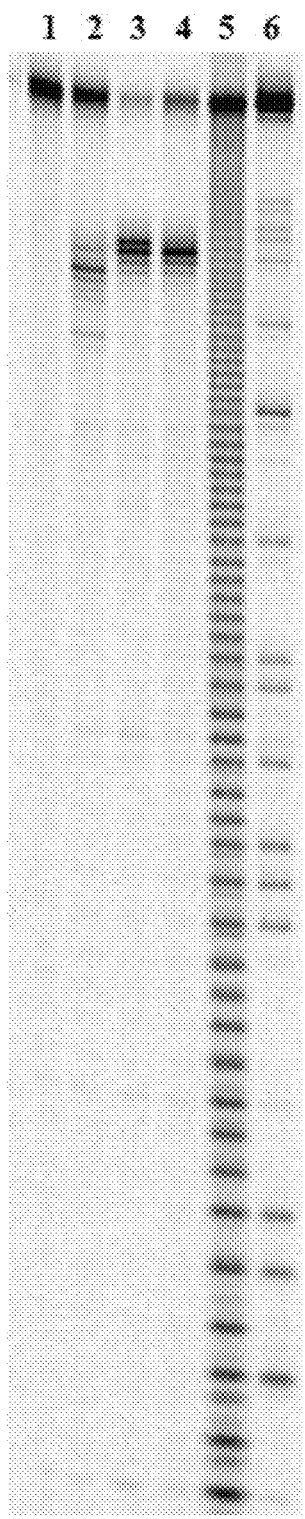

FIG. 6 shows the mapping of cleavage site generated by catAEA-ZfQQR, the GQ variant and the GGKKQ variant on the substrate strand RNA of the DNA-RNA hybrid containing a binding site for zinc finger ZfQQR. Digestion reaction shown in Lanes 1-14 were performed with 0.05 μM of the radioactively labeled substrate, 0.5 μM of non-labeled substrate, 25 mM Tris (pH 8.0), 100 mM KCl, 2 mM DTT, 30 min at 37° C. with presence or not of different enzyme and presence of appropriate concentration of $MgCl_2$ and/or 20 μM $ZnSO_4$ as indicated below. Lane 1: uncleaved substrate, Lane 2: 35 nM of catAEA-ZFQQR, 20 μM $ZnSO_4$, Lane 3: 50 nM of GQ variant, 1 mM $MgCl_2$, 20 μM $ZnSO_4$ Lane 4: 50 nM of GGKKQ variant, 2 mM $MgCl_2$, 20 μM $ZnSO_4$, Lane 5: ribonuclease T1 cleavage of ssRNA, Lane 6: The alkaline hydrolysis of ssRNA substrate.

FIG. 7 illustrates cleavage positions of the substrate DNA-RNA hybrids containing the binding site for zinc finger ZfQQR by the catAEA-ZfQQR, indicated by arrows above the sequence, the larger black arrow indicates the major cleavage site, the smaller arrows additional sites (top strand RNA, the bottom strand DNA, the binding site for ZfQQR marked with box).

FIG. 8 illustrates cleavage positions of the substrate DNA-RNA hybrids containing the binding site for zinc finger ZfQQR by the GQ variant of the catAEA-ZfQQR, indicated by arrows above the sequence, the larger black arrow indicates the major cleavage site, the smaller arrows additional sites (top strand RNA, the bottom strand DNA, the binding site for ZfQQR marked with box).

FIG. 9 illustrates cleavage positions of the substrate DNA-RNA hybrids containing the binding site for zinc finger ZfQQR by the GGKKQ variant of the catAEA-ZfQQR, indicated by arrows above the sequence, the larger black arrow indicates the major cleavage site, the smaller arrows additional sites (top strand RNA, the bottom strand DNA, the binding site for ZfQQR marked with box).

Figures 10, 11:
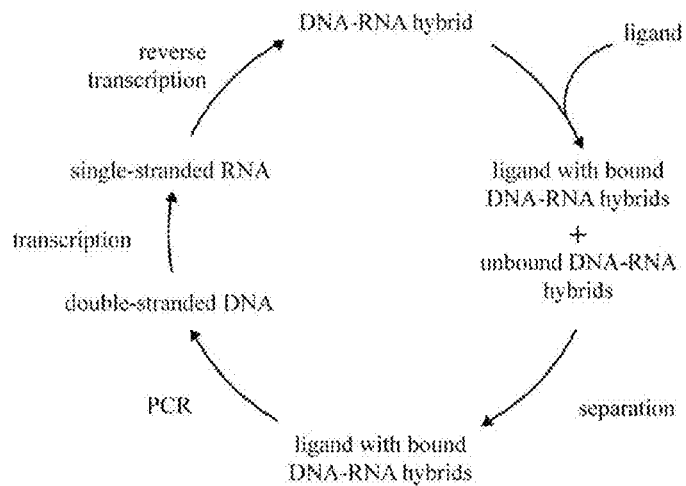

FIG. 10 shows a diagram representing the different stages of one round of SELEX procedure modified according to the invention.

FIG. 11 shows the sequences of DNA oligonucleotide templates for obtaining single-stranded RNA in the process of in vitro transcription using bacteriophage T7 RNA polymerase. The template A (SEQ ID No:26) contains a binding site for zinc finger ZfQQR. The template B (SEQ ID No:27), does not contain binding site for zinc finger ZfQQR and has a unique cleavage site for restriction enzyme XhoI. The template 9N (SEQ ID No:28), contains nine nucleotide degenerate region (single degenerate nucleotide marked "N").

Figure 12:
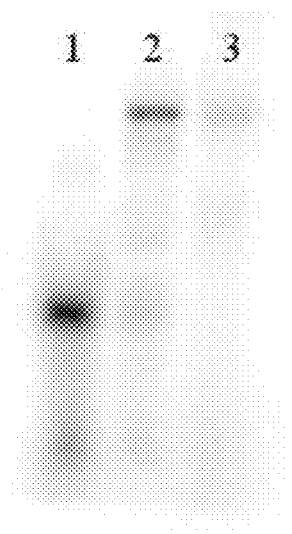

FIG. 12 illustrates the process of obtaining a DNA-RNA hybrid. DNA fragments were resolved in 15% denaturing polyacrylamide gel containing 6 M urea. The 5' ends of 55 nucleotides long DNA oligonucleotide and primer 2 were labeled with radioactive isotope phosphorus 33. Line 1: 0.5 pmol of labeled primer 2 Line 2: 0.25 pmol of reverse transcription product, Line 3: 0.25 pmol of 55 nt labeled DNA oligonucleotide.

Figure 13:
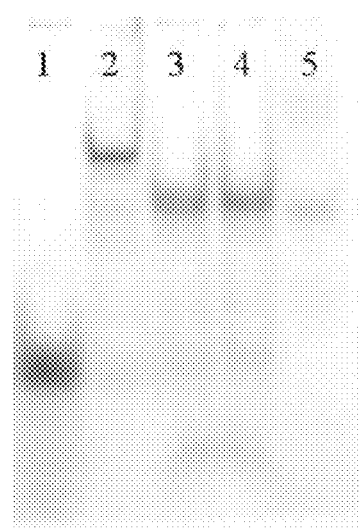

FIG. 13 illustrates the process of obtaining a DNA-RNA hybrid. DNA fragments were resolved in 15% native polyacrylamide gel. The 5' ends of 55 nucleotides long DNA oligonucleotide and primer 2 were labeled with radioactive isotope phosphorus 33. Line 1: 0.5 pmol of labeled primer 2, Line 2: 0.25 pmol of reverse transcription product, Line 3: 0.25 pmol of reverse transcription products digested 5 units of ribonuclease H, Line 4: 0.25 pmol of reverse transcription products digested a unit of ribonuclease H, Line 5: 0.25 pmol of 55 nt labeled DNA oligonucleotide.

Figure 14:
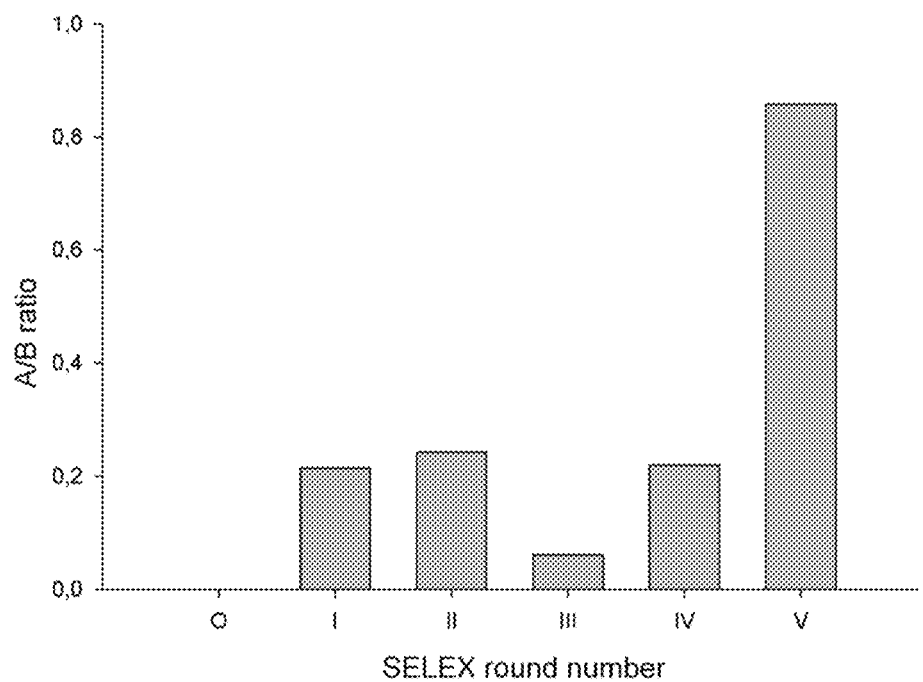

FIG. 14 shows a bar graph illustrating the change in the ratio between double-stranded DNA containing a binding site for zinc finger ZfQQR (A) and double-stranded DNA which doesn't contain a binding site for ZfQQR (B) in successive rounds of the SELEX procedure ("O" means the input, starting mixture of hybrid A with B in the ratio 1:10000, I-V are numbers of successive rounds).

Figures 15, 16:
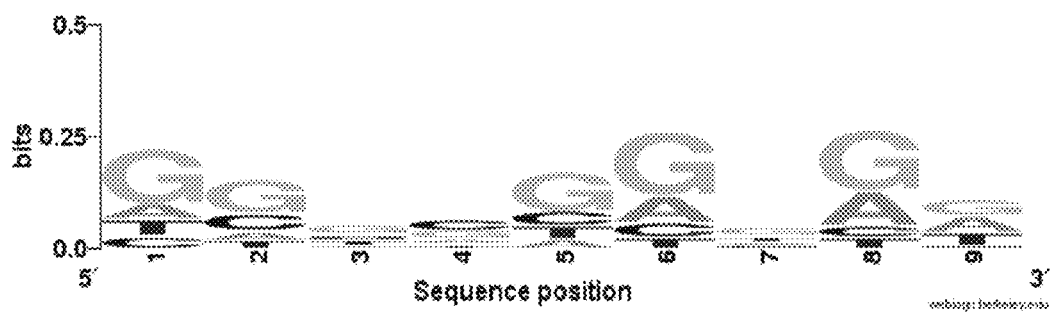

FIG. 15 illustrates a sequence logo derived from 40 sequences using WebLogo.

FIG. 16 shows the sequences of the DNA-RNA hybrids used to determine the $K_D$ constant for the zinc finger ZfQQR, where FIG. 16A is a DNA-RNA hybrid which contains the binding site described in the literature and FIG. 16B is a DNA-RNA hybrid with the sequence consensus after five rounds of SELEX.

Figure 17:
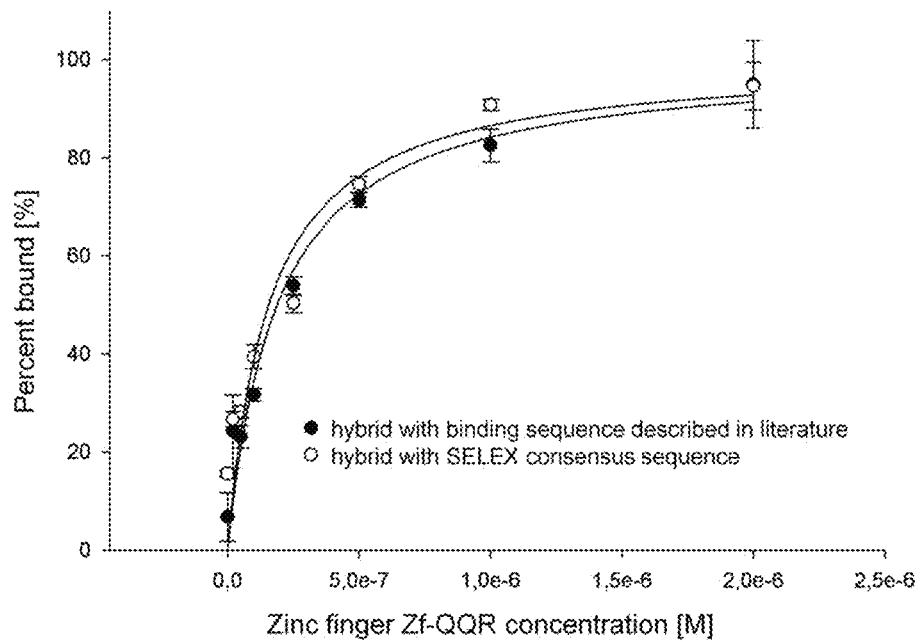

FIG. 17 shows a graph that represents the change of amount of radioactively labeled substrate retained on a nitrocellulose filter, depending on the concentration of zinc finger ZfQQR in the reaction mixture (expressed as percent bound).

DETAILED DESCRIPTION OF THE INVENTION

The inventors have unexpectedly found out that a sequence-specific engineered ribonuclease H that cleaves the RNA strand of the DNA-RNA hybrids in a specific location could be obtained by fusing a catalytic domain of RNase HI or a derivative thereof with a zinc finger DNA-RNA hybrid binding domain, in which the zinc finger binding domain has the ability to bind to specific sequences in the DNA-RNA hybrid.

In the first aspect, the invention provides a ribonuclease which cleaves the RNA strand in DNA-RNA hybrids, wherein the ribonuclease is a fusion protein which may comprise a catalytic domain of RNase HI or a derivative thereof with a zinc finger DNA-RNA hybrid binding domain, and wherein the zinc finger binding domain has the ability to bind to specific sequences in the DNA-RNA hybrid. The preferred ribonuclease is a derivative of the catalytic domain of RNase HI which may comprise a deletion of the RNase HI hybrid binding domain, preferably the catalytic domain of RNase HI is from *Bacillus halodurans*, more preferably may comprise polypeptide encoded by nucleotides 175 to 588 of rnhA gene shown in SEQ ID No:1. In the ribonuclease, the preferred catalytic domain of RNase HI may comprise at least one substitution of one amino acid in the substrate binding region selected from: K81A, K89E and K123A, and preferably contains all substitutions K81A, K89E and K123A.

In the preferred ribonuclease, the zinc finger domain is a derivative of the zinc finger ZfQQR, preferably a polypeptide encoded by nucleotides from 19 to 303 of the sequence ZfQQR shown in SEQ ID No.2. The ribonuclease preferably may comprise fusion protein catAEA-ZfQQR as shown in SEQ ID No.4. The ribonuclease preferably may comprise fusion protein GQ as shown in SEQ ID No.6. The ribonuclease also preferably may comprise fusion protein GGKKQ as shown in SEQ ID No.8.

In the next aspect, the invention provides the composition which may comprise a ribonuclease according to the invention.

The invention also concerns the use of the ribonuclease according to the invention or a composition according to the invention for the cleavage of the RNA strand in DNA-RNA hybrids. In such use, the preferred cleavage of the RNA strand in DNA-RNA hybrids is located 2-16 nucleotides, preferably 5-7 nucleotides, away from the binding site for the zinc finger.

The invention also provides the method of obtaining engineered RNase HI, which cleaves RNA strand in DNA-RNA hybrids which may comprise the following steps:
a) obtaining a RNase HI catalytic domain, that does not bind the substrate but retains the catalytic activity, preferably by removal of binding domains and/or substitution of amino acids involved in substrate binding;
b) obtaining an engineered RNase HI by making fusion protein which may comprise the RNase HI catalytic domain obtained in step a) with binding domain that has the ability to bind to specific sequences in the DNA-RNA hybrid, preferably with zinc finger DNA-RNA hybrid binding domain. In preferred method of obtaining an engineered RNase HI, the zinc finger domain is a derivative of zinc finger ZfQQR, preferably a polypeptide encoded by nucleotides from 19 to 303 of the sequence ZfQQR shown in SEQ ID No.2. In such method the catalytic domain of RNase HI is preferably from *B. halodurans*, preferably may comprise polypeptide encoded by nucleotides 175 to 588 of rnhA gene shown in SEQ ID No:1. The catalytic domain of RNase HI preferably may comprise changes in the substrate binding region, preferably selected from substitution, deletion and/or insertion of at least on amino acid.

The ribonuclease that cleaves the RNA strand of the DNA-RNA hybrids, of the invention contains a fusion of RNase HI or derivative thereof and a DNA-RNA hybrid binding zinc finger, where RNase HI is from *B. halodurans* and the zinc finger has the ability to bind to specific sequences in the hybrid DNA-RNA. Preferably the ribonuclease, according to the invention, is characterized by being a derivative of RNase HI from *B. halodurans*, the catalytic domain polypeptide, even more preferably may comprise a polypeptide encoded by nucleotides 175 to 588 of rnhA gene shown in SEQ ID NO:1. Equally preferably, the ribonuclease according to the invention is characterized by being a derivative of the native RNase HI, which contains a deletion of the DNA-RNA hybrid binding domain. Preferably the ribonuclease, according to the invention, is characterized by being a catalytic domain derivative RNase HI, which contains a substitution of amino acid in the substrate binding region: K81A, K89E and K123A. Most preferably the ribonuclease according to the invention is characterized by being a fusion of the polypeptide encoded by nucleotides 175 to 588 of rnhA gene shown in SEQ ID No. 1 and the zinc finger domain being a derivative of zinc finger ZfQQR, preferably a polypeptide encoded by nucleotides from 19 to 303 zinc finger ZfQQR shown in SEQ ID No. 2.

Sequence-specific ribonuclease H can be used in a specific and localized fragmentation of nucleic acids for RNA mass spectrometry, including studies on modification of RNA. The invention can be use to generate fragments of RNA for third generation sequencing. Sequence-specific engineered RNase H can be used to detect or map viral RNA with specific sequences, where the single-stranded RNA is annealed with DNA, and the resulting hybrid is cleaved. The invention can be used for the engineering of proteins by shuffling fragments and ligation of mRNA, where fragments are obtained by digestion with specific engineered ribonuclease H. The invention can be used to direct site-specific cleavage of persistent DNA-RNA hybrids in vivo.

Enzymes with new features can be obtained by constructing fusions of several domains with different functionality. Engineering of a ribonuclease that cleaves the RNA strand of DNA-RNA hybrid in a sequence-dependent manner is based on the fusion of two proteins domains: engineered RNase HI and a DNA-RNA hybrid binding zinc finger. RNase HI from *B. halodurans* is an enzyme that hydrolyzes the RNA strand in a DNA-RNA hybrid in a sequence-independent manner. The zinc finger ZfQQR has the ability to bind to a well-defined sequence in the DNA-RNA hybrid. In one of the embodiments of the fusion enzyme, the domain which exhibits a ribonuclease activity against the RNA strand in a DNA-RNA hybrid is a fragment of a gene from *B. halodurans* rnhA encoding the catalytic domain (termed cat). It is a fragment from 175 to 588 nucleotide rnhA gene, which corresponds to region from 59 to 196 amino acid residue of the native protein RNase HI from *B. halodurans*. From the native gene a fragment encoding the hybrid binding domain (HBD) was removed, because of its ability to bind DNA-RNA hybrids independently of the sequence. The fusion of the catalytic domain with ZfQQR was termed cat-ZfQQR. The engineered catalytic domain has three amino acid substitutions introduced in the substrate binding region: K81A, K89E and K123A. The substitutions involve the positively charged lysines, which are localized close to the known substrate binding region. Substitutions in the binding site are not intended to inactivate the enzyme, but to cause that the enzyme's substrate binding is dependent upon the presence of the additional DNA-RNA hybrid binding domain. The domain, which confers the sequence specificity of the fusion enzyme, is the zinc finger ZfQQR. In the fusion enzyme, the gene fragment encoding a zinc finger ZfQQR from 19 to 303 nucleotide was used, which corresponds to a region from 7 to 101 amino acid residue of the protein. Additionally, the interdomain linker region of the fusion enzyme was modified to produce two variants, termed GQ and GGKKQ. GQ is the fusion of the catalytic domain with substitutions in K81A, K89E and K123A with ZfQQR that lacks a fragment encoding amino acids in positions 138-148 of the fusion enzyme. GGKKQ is the fusion of the catalytic domain with substitutions in K81A, K89E and K123A with ZfQQR that lacks a fragment encoding amino acids in positions 138-139 and 141-146 of the fusion enzyme. The descriptions of generated constructs are summarized in Table 1.

TABLE 1

Description of constructs, their abbreviation used further and in the examples and their references to SEQ ID NOs.

| Description | Abbreviation | References to SEQ ID NOs |
|---|---|---|
| catalytic domain of RNase HI from *B. halodurans* | cat | fragment coded by nucleotides 175 to 588 of SEQ ID No: 1 |
| the fusion of catalytic domain with ZfQQR | cat-ZfQQR | fragment coded by nucleotides 175 to 588 of SEQ ID No: 1 and nucleotide 19 to 303 of SEQ ID No: 2 |
| the fusion of the catalytic domain with substitutions in K81A, K89E and K123A with ZfQQR | catAEA-ZfQQR | construct coded by SEQ ID No: 3 (nucleotide sequence) and shown SEQ ID No: 4 (amino acid sequence) |
| the fusion of catalytic domain with substitutions introducing changes in the amino acid sequence of protein in positions K81A, K89E and K123A with zinc finger ZfQQR and the interdomain linker shortened by a fragment encoding amino acids in positions 138-148 | GQ | construct coded by SEQ ID No: 5 (nucleotide sequence) and shown SEQ ID No: 6 (amino acid sequence) |
| the fusion of catalytic domain with substitutions introducing changes in the amino acid sequence of protein in positions K81A, K89E and K123A with zinc finger ZfQQR and the inter domain linker shortened by a fragment encoding amino acids in positions 138-139 and 141-146 | GGKKQ | construct coded by SEQ ID No: 7 (nucleotide sequence) and shown SEQ ID No: 8 (amino acid sequence) |

In the next aspect the invention also provides the method of determining the substrate preference of DNA-RNA hybrid binding protein(s) or its domain(s). Such a method allows to determine the preferred sequence recognized by a protein(s) or its domain(s) and/or bound by a protein domain in the DNA-RNA hybrid.

The invention provides method of determining the sequence preference of DNA-RNA hybrid binding protein(s) or its domain(s), in which the method may comprise the following steps:
a) contacting of the purified protein or its domain, with a mixture of a library of DNA-RNA hybrids substrates, wherein DNA-RNA hybrids substrates may comprise randomized sequences in the central part, preferably randomized 9 or 10 nucleotide positions, with flanking sequences fixed and allowing a tested protein or its domain to bind with the sequence to which it has an affinity;
b) separating unbound DNA-RNA hybrids by immobilization of protein or its domain, with bound DNA-RNA hybrid, to the resin, preferably glutathione agarose;
c) removing the unbound hybrids;
d) isolating the recombinant protein, together with the associated DNA-RNA hybrids, preferably by adding a buffer containing glutathione;
e) amplification of isolated hybrid using PCR, preferably RT-PCR, wherein in the amplification reaction the primers complementary to known sequences on the flanking sequences of the randomized region are used, and wherein during the PCR reaction on one of the primer the sequence of RNA polymerase promoter is added in order to obtain double-stranded DNA for in vitro transcription with RNA polymerase;
f) reverse transcription is performed using reverse transcriptase that does not possess the RNase H activity and a DNA primer complimentary to 3' end of the RNA template in order to obtain a DNA-RNA hybrid, and steps a) to f) are preferably repeated.

In preferred embodiment of the method promoter sequence may comprise the promoter sequence for T7 RNA polymerase and RNA polymerase is T7 RNA polymerase. Preferably, the protein or its domain is a recombinant protein or recombinant domain. Protein or its domain preferably may comprise zinc finger(s). In preferred embodiment the protein or its domain is the fusion of the zinc finger domain and GST, preferably the fusion of the zinc finger domain and GST encoded by SEQ ID No:37. The preferred protein or its domain is the fusion of RNase HI or a derivative thereof, preferably RNase HI is from *B. halodurans*, preferably which may comprise a polypeptide encoded by nucleotides 175 to 588 of rnhA gene shown in SEQ ID No:1, and a zinc finger. The zinc finger has preferably the ability to bind to specific sequence in the DNA-RNA hybrid, the prefer zinc finger is ZfQQR, preferably of sequence encoded by nucleotides from 19 to 303 of the sequence ZfQQR shown in SEQ ID No.2.

As further aspect the invention provides method of obtaining library of DNA-RNA hybrids which may comprise the flowing steps:
a) PCR amplification of the library of DNA oligonucleotides containing a degenerate sequence in the central position, flanked by invariant sequences, which include a promoter sequence for RNA polymerase,
b) synthesis of RNA strand using RNA polymerase on the obtained in a) double stranded DNA as a template,
c) reverse transcription of the primer complementary to the invariant sequence present at the 3' end of RNA obtained in b) with a reverse transcriptase that does not possess a RNase H activity, wherein during reverse transcription the RNA strand is not degraded, and the hybrid consisting of a fully complementary RNA and DNA strands are obtained. Preferably, in such method the oligonucleotides contain a degenerate sequence in the central position which may comprise randomized 9 or 10 nucleotide positions. Even more preferably the promoter sequence may comprise the promoter sequence for T7 RNA polymerase and RNA polymerase is T7 RNA polymerase.

To determine the full range of sequences recognized by a sequence-specific DNA-RNA hybrid binding protein and the substrate preference of DNA-RNA hybrid binding protein(s) or its domain(s), in the DNA-RNA hybrids, as described in the invention, a modification of the SELEX method was developed, which enables iterative cycles of selection of a DNA-RNA hybrid sequence preferentially bound by a protein (FIG. 10). A new element in this process is the way of amplification and recreation of a library of DNA-RNA hybrids, in order to be used in the next cycle. It involves using PCR amplification of a library of DNA oligonucleotides containing a degenerate sequence in the central position, flanked by invariant sequences, which include a promoter sequence for RNA polymerase, preferably T7 RNA polymerase. The resulting double stranded DNA is used as a template for the synthesis of RNA strand using RNA polymerase, preferably T7 RNA polymerase. A pool of single-stranded RNA is obtained and serves as a template for reverse transcription in order to obtain a library of DNA-RNA hybrids. Reverse transcriptase extends the primer complementary to the invariant sequence present at the 3' end of RNA. During reverse transcription by an enzyme with removed ribonuclease H activity (the reverse transcriptase that does not possess ribonuclease H activity), the RNA strand is not degraded, allowing for the creation of a hybrid consisting of a fully complementary RNA and DNA strands. A library of DNA-RNA hybrids is obtained in this way, because the template RNA was heterogeneous in the central part of the sequence. The effectiveness of the developed modification of SELEX method was confirmed using zinc finger ZfQQR as ligand, which binds DNA-RNA hybrid. ZFQQR was obtained as a result of engineering and binds the 5 'GGGGAAGAA-3' sequence in the DNA strand of DNA-RNA hybrids (Shi and Berg, Specific DNA-RNA hybrid binding by zinc finger proteins. 1995. Science, vol. 268) For this example, the ZFQQR fusion with Glutathione S-transferase domain (called GST) was used.

In the following examples, unless otherwise indicated standard materials and methods are used as described in Sambrook J. et al., "Molecular Cloning: A Laboratory Manual, 2nd edition. 1989. Cold Spring Harbor, N.Y. Cold Spring Harbor Laboratory Press, or proceeding in accordance with manufacturers' recommendations for specific materials and methods. As used herein, unless otherwise indicated by standard abbreviations for amino acids and nucleotides or ribonucleotides.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example 1

Cloning of the rnhA Gene Fragment from *Bacillus halodurans* into the Expression Vector pET 30b The vector pET15a carrying the rnhA gene (SEQ ID NO:1) (SEQ ID NO:1 is DNA sequence of rnhA RNase HI (Gene ID 893801, BH0863) from *B. halodurans* and was obtained from private sources. A fragment of the gene encoding cat (catalytic domain) was amplified by using PCR technique in standard conditions performed on the pET15a carrying the rnhA gene as the template and 1 U of Phusion polymerase (New England Biolabs) with 50 pmol of each primer Bhcatr (SEQ ID No:12) and Bhcatf (SEQ ID No:11) (see FIG. 1) DNA encoding the rnhA gene fragment corresponding to 175-588 nucleotide and vector DNA pET 30b (Novagen company) was digested with NdeI and KpnI (Fermentas). The reaction mixture containing the DNA was separated on 0.7% agarose gel in TAE buffer and the fragments corresponding to the expected sizes 430 bp and 5313 bp, respectively, were reisolated from the gel using a kit for reisolation (Gel out, A & A Biotechnology). Then, 50 ng reisolated rnhA gene fragment and 25 ng of cut vector pET 30b was treated with bacteriophage T4 DNA ligase (Fermentas) and ligase was heat inactivated. Then the ligation mixture was used for bacterial cell transformation. *E. coli* competent bacteria (Top10 (Invitrogen)), have been transformed with ligation mixture (20-200 ng per 50 µl of bacterial cells). The transformants were selected on on LB-agar plates supplemented with 30 µg/ml kanamycin. The selection of transformants containing the desired recombinants was based on analysis of restriction maps, and then the samples were sequenced to confirm the sequence of constructs.

Example 2

Cloning of the Gene Encoding a Zinc Finger ZfQQR to the Expression Vector pET28b Synthesis of the gene encoding the zinc finger ZfQQR was ordered from Epoch's Life Sciences (see SEQ ID No:2 which is the sequence of the synthesized DNA of a zinc finger ZFQQR gene) on the basis of the amino acid sequence from the article "Shi Y, Berg J M. Specific DNA-RNA hybrid binding proteins. Science. 1995. vol. 268, 282-284). DNA encoding ZfQQR and DNA vector pET28b (Novagen company) was digested with restriction enzymes NcoI and XhoI (enzymes were from Fermentas Company, reactions were carried out in a buffer 2× Yellow according to the manufacturer's instructions, 1 unit of enzyme per 1 mg DNA for 1 h in 37° C.). The reaction mixture was separated on 0.7% agarose gel in TAE buffer and treated as in Example 1. Then, 50 ng of the reisolated ZfQQR gene and 25 ng of the digested vector pET28b were ligated by T4 DNA ligase (Fermentas, the reaction carried out in buffer supplied by the manufacturer) at room temperature for 1 hour. Ligase was heat inactivated by incubation at 75° C. for 10 min. Then the ligation mixture was used to transform bacterial cells as in Example 1.

Example 3

Cloning of the Gene Encoding the Zinc Finger ZfQQR to the Expression Vector pET 30b Containing a Fragment of a Gene from *Bacillus halodurans* rnhA A fragment of the gene encoding ZfQQR from the vector pET28b was amplified by the PCR technique. The reaction was carried out in standard conditions performed on the pET28b carrying the ZfQQR gene as the template and 1 U of Phusion polymerase (New England Biolabs) with 50 pmol of each primer BbZf (SEQ ID No:13) and Kmr (SEQ ID No:15) (see FIG. 1). A fragment of the gene encoding the catalytic domain of RNase HI in vector pET 30b was amplified by the PCR technique. The reaction was carried out in standard conditions performed on the pET 30b carrying the cat gene as the template and 1 U of Phusion polymerase (New England Biolabs) with 50 pmol of each primer Kmf (SEQ ID No:14) and Bhcatr (SEQ ID No:12) (see FIG. 1). The purified PCR products were phosphorylated with bacteriophage T4 polynucleotide kinase (Fermentas). DNA from both reactions (20 ng) were combined, ligated and ligation mixtures were transformed into bacterial cells as in Example 1.

Example 4

Mutagenesis of the Gene Encoding the Fusion Enzyme that Introduces Amino Acid Substitutions at Positions K81A, K89E and K123A The ligation of the fragments generated in Example 3 created a construct where the open reading frame contained in the beginning a part of the gene encoding cat and the gene fragment encoding ZfQQR at the end. The obtained DNA construct served as a template to introduce substitutions using PCR technique in the nucleotides encoding amino acid residues at positions 81, 89 and 123 of the protein. Substitutions were introduced in stages, first were substituted nucleotides encoding residues 81 (lysine to alanine substitution) and 89 (substitution of lysine for glutamic acid), only after obtaining such a construct, PCR was carried out to convert the nucleotides encoding the residue in position 123 (substitution of lysine to alanine). The PCR reaction was carried out in standard conditions performed on the pET30b carrying the cat-ZfQQR gene as the template and 1 U of Phusion polymerase (New England Biolabs) with 50 pmol of each primer K81Af (SEQ ID No:17), K81 Ar (SEQ ID No:16), K89Ef (SEQ ID No:19), K89Er (SEQ ID No:18), K123Af (SEQ ID No:21) and K123Ar (SEQ ID No:20) (see FIG. 1):

The purified PCR products were treated as in Example 1 and ligation mixtures were transformed into bacterial cells. The final sequence of the gene encoding the catAEA-ZfQQR is shown in SEQ ID No:3 and the resulting amino acid sequence of the protein sequence is shown in SEQ ID No:4.

Example 5

Mutagenesis of the Gene Encoding the Fusion Enzyme with Amino Acid Substitutions at Positions K81A, K89E and K123A that Shortens the Length of the Interdomain Linker Region The construct generated in Example 4 carries the open reading frame encoding the catAEA-ZfQQR at the end and served as a template to shorten the interdomain linker using PCR technique in the region encoding the interdomain linker 409-449 in the gene on SEQ ID No:3. The PCR reaction was carried out in standard conditions performed on the pET30b carrying the catAEA-ZfQQR gene as the template and 1 U of Phusion polymerase (New England Biolabs) with 50 pmol of each primer del11f (SEQ ID No:22) and del11r (SEQ ID No:23) (which were used to generate variant named as GQ), or primers del5f (SEQ ID No:24) and del5r (SEQ ID No:25) (which were used to generate variant named as GGKKQ) respectively (see FIG. 1 for primers sequences).

The purified PCR products were treated as in Example 1 and ligation mixtures were transformed into bacterial cells. The final sequence of the gene encoding the variant GQ that is the catAEA-ZfQQR with inter domain linker shortened by a fragment encoding amino acids in positions 138-148 shown in SEQ ID No:5 and the resulting amino acid sequence of the protein sequence shown in SEQ ID No:6. The final sequence of the gene encoding the variant GGKKQ that is the catAEA-ZfQQR with the inter domain linker shortened by a fragment encoding amino acids in positions 138-139 and 141-146 shown in SEQ ID No:7 and the resulting amino acid sequence of the protein sequence shown in SEQ ID No:8.

Example 6

Expression and Purification of Proteins by Ion Exchange Chromatography

Plasmid pET15a with the gene encoding the full length RNase HI from B. halodurans, pET 30b with the gene encoding cat, pET 30b with the gene encoding the catAEA-ZfQQR and pET 30b with the gene encoding variant GQ and pET30 with the gene encoding variant GGKKQ were each transformed into E. coli strain ER2566 (New England Biolabs). The protein expression was induced with IPTG and proteins were purified according to standard protocol on Ni-NTA resin (Sigma Aldrich).

Example 7

Nuclease Activity Assay of the Fusion Enzyme

The effect of the presence of magnesium and zinc ions in reaction on the enzymatic activity and specificity of the full-length RNase HI from B. halodurans, cat, cat-ZfQQR and catAEA-ZfQQR was tested. The activity assay included the presence of 5 mM $MgCl_2$ and/or 20 μM $ZnSO_4$. The 5' end of the RNA strand in the substrate DNA-RNA hybrid was labeled with radioactive isotope phosphorus 33. Digestion reaction contained 0.05 μM radiolabeled substrate and 0.5 μM unlabeled substrate:

```
RNA:
                                        (SEQ ID No: 9)
AGAACUAGUGGAUCAACCGGGCUGCAGGAAUUCGAUAUCAAGCU

UAUCGAUACCGUGGCGGUUCUUCCCCAAGCC

DNA:
                                        (SEQ ID No: 10)
GCTTGGGGAAGAACCGCCACGGTATCGATAAGCTTGATATCGAATT

CCTGCAGCCCGGTTGATCCACTAGTTCT
``` and 25 mM Tris (pH 8.0), 100 mM KCl, 5 mM $MgCl_2$ and/or 20 μM $ZnSO_4$, 2 mM DTT. Reactions contained: 12.5 nM of the full-length RNase HI from B. halodurans, 625 nM of cat, 5 nM of the cat-ZfQQR or 25 nM of catAEA-ZfQQR. Digestion reactions were carried out in 37° C. and stopped after 30 min by adding formamide to a final concentration of 50%. The digestion products were resolved in 12% denaturing polyacrylamide gel containing 6 M urea (see FIG. 3). The gel was dried on a vacuum drier and exposed to Storage Phosphor Screens (GE Healthcare) overnight. The audioradiogram was scanned on a Typhoon Trio scanner (GE Healthcare).

In the presence of 20 μM $ZnSO_4$, and in the absence of $MgCl_2$ the substrate digestion by the catAEA-ZfQQR generates products of unique size. Cleavage in this place does not occur when such a substrate is digested by the full-length RNase HI from B. halodurans, cat and cat-ZfQQR.

The effect of linker length reduction on the specificity of the substrate cleavage by variants GQ and GGKKQ was determined. The conditions assayed included a range of magnesium ion concentration in the presence of zinc in the reaction. The activity assay included the presence of a range of 0.05 mM to 10 mM $MgCl_2$ and 20 µM $ZnSO_4$ and buffer composition as above. The 5' end of the RNA strand in the substrate DNA-RNA hybrid was labeled with radioactive isotope phosphorus 33. Digestion reaction contained 0.05 µM radiolabeled substrate and 0.5 µM unlabeled substrate (FIG. 2), 25 mM Tris (pH 8.0), 100 mM KCl, 5 mM $MgCl_2$ and 20 µM $ZnSO_4$, 2 mM DTT. In the reaction, 50 nM of variant GQ and 50 nM of variant GGKKQ was used. Digestion reactions were carried out as above and result are shown on FIG. 4 for GQ and FIG. 5 for GGKKQ. For the GQ variant of the linker, the optimal concentration of $Mg^{2+}$ in the reaction was 1 mM and for the GGKKQ variant it was 2 mM.

In order to accurately determine the cleavage site in the DNA-RNA hybrid substrate that contains a binding site for zinc finger ZfQQR generated by the catAEA-ZfQQR and its GQ and GGKKQ variants, the cleavage products were separated in a polyacrylamide gel with a resolution allowing the separation of fragments differing by one nucleotide. The 5' end of the RNA strand in the substrate DNA-RNA hybrid was labeled with radioactive isotope phosphorus 33. The digestion reaction contained 0.05 µM radiolabeled substrate and 0.5 µM unlabeled substrate (see FIG. 2), 25 mM Tris (pH 8.0), 100 mM KCl, 20 µM $ZnSO_4$, 1 mM $MgCl_2$ (in case of variant GQ) and 2 mM $MgCl_2$ (in case of variant GGKKQ) and 2 mM DTT. The reaction contained 0.1 µM catAEA-ZfQQR, 50 nM of variant GQ and 50 nM of variant GGKKQ. Digestion reactions were carried out at 37° C. and stopped after 1 h by adding formamide to a final concentration of 50%. Size marker with fragments differing by one nucleotide was obtained by alkaline hydrolysis according to Ambion's recommendations (www.ambion.com). The digestion products were resolved in 12% denaturing polyacrylamide gel containing 6 M urea (see FIG. 6). The resulting fragments of the identified sequence length was mapped on the sequence of the substrate and determined that the main product of cleavage for the catAEA-ZfQQR has the length of 54 nucleotides (see FIG. 7). It is located on the opposite strand 7 nucleotides away from the binding site for zinc finger ZfQQR. In case of the GQ and GGKKQ, the main product of cleavage has the length of 56 nucleotides (see FIG. 8 for GQ and FIG. 9 for GGKKQ) and it is located on the opposite strand 5 nucleotides away from the binding site for zinc finger ZfQQR.

The new ribonuclease of invention cleaves the RNA strand in DNA-RNA hybrids, and is fusion protein which may comprise the catalytic domain of ribonuclease HI (RNase HI) with a zinc finger DNA-RNA hybrid binding domain, wherein the zinc finger binding domain has the ability to bind to specific sequences in the DNA-RNA hybrid. The preferred obtained fusion proteins are catAEA-ZfQQR, GQ, GGKKQ.

It was not obvious that a sequence-specific engineered RNase H could be obtained by fusing a RNase HI domain and a zinc finger because the nuclease domain is a processive enzyme that upon binding to the substrate cleaves multiple times in several places of the substrate. Moreover, as it was described earlier, the fusion of an unchanged RNase H to a zinc finger does not allow to obtain a sequence-specific enzymes well as the fusion of the cat fragment of RNase HI does not allow to obtain a sequence-specific enzyme. Not to be bound by any theory there are few possible reasons for this—the RNase HI is a processive enzyme that will always cleave in multiple times, the zinc finger in fusion with other domains does not bind its binding sequence in DNA-RNA hybrids, the cleavage conditions were not optimal, the cat domain binds the substrate regardless of the presence of the zinc finger or all of them were important.

Moreover, it was not obvious that the substitutions in the substrate binding region: K81A, K89E and K123A of cat would lead to a sequence-specific enzyme. There are several hypothesis that may provide an explanation for not obtaining a specific: the cat domain can bind the substrate regardless of the presence of the zinc domain, or substitutions in the binding region could have affected the catalysis of the enzyme and produced a variant that is inactive, or substitutions of amino acids in proteins can lead to variants that cannot fold properly and thus that are not soluble. There was no data or suggestions available in prior art that would allow to be certain that the destabilization of binding by the cat domain would enable to obtain an enzyme that cleaves in a defined distance from the binding site.

Example 8

Preparation of Substrate DNA-RNA Hybrids

Three 78 nucleotide long single-stranded DNA were synthesized named: template A (SEQ ID No:26), template B (SEQ ID No:27) and template 9N (SEQ ID No:28), respectively.

These oligonucleotides were used as a template to create double-stranded DNA using the PCR technique. The reaction was carried out in standard conditions, approximately 0.1 pmol template and 1 unit of Phusion polymerase (New England Biolabs) with 10 pmol of each primer 1 and 2:

```
primer 1:
                                        (SEQ ID No: 33)
AATTTAATACGACTCACTATAGGGCTCTAGATCTCACTAAGCATAG primer 2:
                                        (SEQ ID No: 34)
GAGATCTAGACGGAACATG
```

Primers 1 and 2 were used for amplification of double-stranded DNA in the PCR reaction and primer 2 was also used in reverse transcription reaction.

Reaction conditions: initial denaturation of 98° C. 1 min, followed by 15 cycles of 15 s denaturation at 98° C., 15 s, renaturation at 72° C. (a reduction of the temperature of renaturation with each cycle by 1° C. to final temperature of 58° C.) and 2 s extension at 72° C., followed by 10 cycles of 15 s denaturation at 98° C., 15 s renaturation at 58° C. and 2 s extension at 72° C. The reaction mixture was extracted with phenol and the collected aqueous phase was precipitated with 0.5 M sodium acetate pH 4.5 and ethanol. The precipitate was air dried and resuspended in water. Single-stranded RNA transcripts were obtained on a double-stranded DNA template with the promoter sequence for bacteriophage T7 RNA polymerase by using a kit for transcription MEGAshortscript™ T7 (Ambion). The reaction was carried out in standard conditions with 200-500 ng of DNA. Transcription reaction was resolved in 15% denaturing polyacrylamide gel containing 6 M urea and TBE buffer and visualized using ethidium bromide under UV light. A band corresponding to the length of 55 nucleotides was excised and elution of RNA from the gel was performed according to standard procedures using Costar Spin X columns (Corning Life Sciences).

DNA-RNA hybrid was obtained on a template of single-stranded RNA using reverse transcriptase with removed RNase H activity. 200 pmol of primer 2 ((SEQ ID NO.34) and 200 pmol of single-stranded RNA was incubated 2 min at 70° C., followed by 2 min on ice. The prepared template was subjected to reverse transcription. The reaction was carried out in 40 μl in a buffer supplied by the manufacturer, with a final concentration of 1 mM dNTP mix, 200 pmol of primer annealed template, 40 units RiboLock (Fermentas) and 400 units RevertAid H minus reverse transcriptase (Fermentas) for 2 h at 42° C. The DNA-RNA hybrids from the reaction mixture were separated from the buffer and dNTPs by using the G-25 rasin (Sigma Aldrich) in a standard procedure.

In order to confirm that the developed protocol leads to the formation of complimentary DNA-RNA hybrids, reverse transcription was performed (description as above) using a radioactively labeled with isotope phosphorus 33 primer 2 (SEQ ID No:34). The synthesis of the appropriate size of DNA (the expected length is 55 nucleotides) was confirmed by comparing the size of the resulting DNA and a control 55 nucleotides long DNA oligonucleotide. Samples were resolved in 15% denaturing polyacrylamide gel containing 6 M urea in TBE buffer (see FIG. 12). The gel was dried on a vacuum drier and exposed to Storage Phosphor Screens (GE Healthcare) overnight. The audioradiogram was scanned on a Typhoon Trio scanner (GE Healthcare). The creation of DNA-RNA hybrids was confirmed by digesting the product of reverse transcription by ribonuclease H and comparing the migration of the product of the reaction with control 55 nucleotides long DNA oligonucleotide in 15% native polyacrylamide gel in TBE buffer (see FIG. 13). Digestion of RNA strands of the DNA-RNA hybrids was carried out in 10 μl in the buffer supplied by the manufacturer with 1 and 5 units of RNase H (Fermentas) for 30 min at 37° C.

Example 9

Cloning, Expression and Purification of GST Fusion Protein with the Zinc Finger ZfQQR In order to obtain the fusion of the zinc finger domain with GST, a gene encoding ZFQQR was cloned into the expression vector pGEX-4T-1 (Amersham). The synthesis of the gene encoding the zinc finger ZfQQR was ordered from Epoch's Life Sciences on the basis of the amino acid sequence from the article "Shi Y, Berg J M. Specific DNA-RNA hybrid binding proteins. Science. 1995. vol. 268, 282-284). DNA encoding ZfQQR was amplified using PCR technique. The primer ZFf and ZFr were synthesized and used for preparation of DNA construct of the fusion of genes encoding the GST domain and zinc finger ZfQQR, The reaction was carried out in standard conditions and 1 unit of Phusion polymerase (New England Biolabs) with 50 pmol of each primer ZFf and ZFr:

```
ZFf: GGTTCTGGTGACCCGGG          (SEQ ID No: 35)

ZFr: CGGGAAAACAGCATTCCAGGTATTAG (SEQ ID No: 36)
```

DNA encoding the zinc finger ZfQQR and the vector pGEX-4T-1 DNA was digested with restriction enzymes SmaI and XhoI (Fermentas). SmaI digestion was performed in a buffer 1× Yellow according to the manufacturer recommendations. After this time the buffer was added to a final concentration 2× Yellow in the reaction, 1 unit of enzyme XhoI for 1 mg DNA for 1 h at 37° C. The reaction was separated on 0.7% agarose gel in TAE buffer and the fragments corresponding to the expected sizes were reisolated from the gel using a kit for the reisolation from the agarose gels (Gel Out, A & A Biotechnology). Then, 50 ng of the reisolated DNA encoding zinc finger ZfQQR and 25 ng of the cut vector pGEX-4T-1 was ligated with bacteriophage T4 DNA ligase (Fermentas, the reaction carried out in manufacturer supplied buffer) at room temperature for 1 hour. Ligase was heat inactivated by incubating at 75° C. for 10 min. Then the ligation mixture was used for transformation into a bacterial strain E. coli Top10 F (Invitrogen). The transformants were selected on 100 μg/ml ampicillin. The selection of suitable transformants containing the desired recombinants was based on analysis of restriction maps, and then the clones were sequenced to confirm the sequence of constructs.

The plasmid pGEX-4T-1 gene encoding the zinc finger ZfQQR transformed into E. coli strain BL21 (DE3): (Promega). Transformants from overnight culture were inoculated into liquid LB with 100 mg/ml ampicillin, and incubated at 37° C. for 2 h. After this time, IPTG was added (final concentration 1 mM) and the culture was incubated with shaking at 25° C. for additional 5 hours. After induction the cultures were centrifuged at 4000 rpm at 4° C. for 10 min washed with 2 ml of STE, centrifuged 10,000 g 10 min. The resulting pellet from culture was resuspended in 35 ml PBS and then bacterial cells were disintegrated by single passage through the French press (Constant Systems LTD) at 1360 atmospheres. Lysates were clarified by centrifugation in the ultracentrifuge at 20 000 g at 4° C. for 20 min. The protein was purified on Gluthathione Sepharose rasin (GE Healthcare) according to standard procedures.

Example 10

Binding of Protein to DNA-RNA Hybrid, Separation of Unbound Hybrids and Elution of the Protein-DNA-RNA Hybrid Complex from the Resin The binding reaction of DNA-RNA hybrid to zinc finger ZfQQR was performed in 40 μl and contained: 200 pmol of DNA-RNA hybrids, 1 pmol of GST fusion with the zinc finger ZfQQR, 25 mM Tris pH 8.0, 100 mM KCl, 20 μM ZnSO$_4$, 2 mM DTT. The reaction was carried out in room temperature for 30 min. After this time the reaction was added to 7.5 μl of Gluthathione Sepharose resin and incubated for 30 min at Thermomixer compact (Eppendorf) at 22° C. with shaking (1,400 rpm). In the next stage, the resin was washed three times with 100 μl buffer P (25 mM Tris pH 8.0, 100 mM KCl, 20 μM ZnSO$_4$, 2 mM DTT), each time the sample was centrifugation at 1000 g for 2 min at room temperature and the supernatant removed. The next step was elution, which was repeated twice with 30 μl buffer E and 10 min incubation at room temperature. After each incubation, the sample was centrifuged at 1000 g for 2 min at room temperature and the supernatant was transferred to a tube. 5 μl of the eluate containing the GST fusion with the zinc finger associated with the DNA-RNA hybrid was subjected to amplification using PCR in order to obtain double-stranded DNA, then RNA was transcribed and DNA-RNA hybrids were synthesized by reverse transcription as in Example 8. Obtained DNA-RNA hybrid was the starting material for the next round of SELEX.

Example 11

Control SELEX

A control of the SELEX method was performed on a mixture of DNA-RNA hybrids containing the binding site for zinc finger ZfQQR (hybrid A, is formed on a template A SEQ ID No:26) and a hybrid, which does not have such a binding site, instead a XhoI restriction site (B hybrid, is created the template B SEQ ID No:27). Five rounds of SELEX was conducted on a control pool consisting of a mixture of hybrids A and B in the ratio 1:10000. In order to distinguish the two sequences, 100 ng of DNA resulting from PCR amplification of the eluate after each round was digested with 2 units of enzyme XhoI 16 h at 37° C. Digestion products were separated on 15% native polyacrylamide gel in TBE buffer. The gel was incubated 2 min in a solution of ethidium bromide at a final concentration of 0.5 μg/ml. The bands were visualized under UV light using a CCD camera for digital archiving of images MultiImager Fluoro-S (BioRad). The intensity of bands corresponding to the size of uncleaved DNA (78 bp) and the digestion products (55 and 23 base pairs) was measured using Quantity One (BioRad) and the relative proportions of the DNA obtained on a template of DNA-RNA hybrids after each round was calculated (see FIG. 14). After five rounds of selection with the fusion of GST and the zinc finger ZfQQR, the proportions of DNA carrying the binding site for ZfQQR and without such a sequence have changed to 1:1,7. This means that by performing SELEX procedure, the pool of control sequences was enriched 8500 times by a sequence specifically bound by ZfQQR.

Example 12

In the SELEX Library RNA-DNA Hybrids

In the next stage, the library of DNA-RNA hybrids containing a central random sequence (generated on the template 9N—SEQ ID No:28) was used to conduct the SELEX procedure and determine the sequence preference of the zinc finger ZfQQR as in Example 11. In order to determine the sequence of selected hybrids 500 ng of DNA PCR product obtained on the template of the eluate after the five rounds of SELEX was digested with 5 units of XbaI enzyme (Fermentas) in buffer supplied by the manufacturer. Digestion products were separated on 15% native polyacrylamide gel in TBE buffer. The band corresponding to the fragment length of 43 base pairs was excised and isolated from the gel according to standard procedures. In order to obtain concatamers, 100 ng of digested DNA fragments were ligated with bacteriophage T4 DNA ligase (Fermentas) in buffer supplied by the manufacturer at room temperature for 3 hours. Ligase was heat inactivated by incubating at 75° C. for 10 min. 200 ng of DNA plasmid vector pUC18 (Fermentas) was digested with XbaI enzyme in the buffer supplied by the manufacturer for 3 h at 37° C. The reaction mixture was separated on 0.7% agarose gel in TAE and the fragments corresponding to the sizes expected reisolated from the gel using a kit for reisolation from agarose gels (Gel out, A & A Biotechnology). Such prepared vector and concatamers were ligated and then transformed into a bacterial strain. The selection of suitable transformants containing the desired recombinants was based on an analysis of the colony color and 12 clones were sequenced and found to contain a total of 42 fragments obtained by the SELEX procedure as indicated in the Table 2.

TABLE 2

The sequences obtained in the SELEX procedure acquired after sequencing the DNA obtained on a template of DNA-RNA hybrid at the end of five rounds of the modified SELEX procedure performed on the zinc finger ZfQQR and a library of sequences containing 9 nucleotide degenerate region.

| Number | Sequence of library |
|---|---|
| 1 | TGGGGACGC |
| 2 | AGTGCTCGA |
| 3 | GACGCATGG |
| 4 | GGTCTGGAG |
| 5 | GAGCGGGAA |
| 6 | TCGTTGCAT |
| 7 | CTAGCGGGT |
| 8 | GCCAGCGAG |
| 9 | AGAGGGGCA |
| 10 | TGGCAGGTT |
| 11 | GGGTGGGAG |
| 12 | GGTCCGGGC |
| 13 | CTCCGATCA |
| 14 | GCAAATGAA |
| 15 | GGGCGGCGT |
| 16 | ACTCTGAGA |
| 17 | TGGGAATGG |
| 18 | AGCGGAGGG |
| 19 | GGATGGAAA |
| 20 | GGGCTGTCA |
| 21 | ACTCCTGAG |
| 22 | GTCAGATGT |
| 23 | GAGATCAGT |
| 24 | GCCGAGCGG |
| 25 | GCTCGGTGA |
| 26 | CGTAGGGAA |
| 27 | GTCGGATGG |
| 28 | CAGCGGGGT |
| 29 | GGGGGGAGG |
| 30 | TCGGCCAAG |
| 31 | CATGTGTTG |
| 32 | GACTGTAGA |
| 33 | CTGCCTGAA |
| 34 | CGGCGGAGA |
| 35 | CGTACAAGG |
| 36 | GGTGGTTGA |
| 37 | ATCAGGGGG |
| 38 | TTGGCGGGG |

TABLE 2-continued

The sequences obtained in the SELEX procedure acquired after sequencing the DNA obtained on a template of DNA-RNA hybrid at the end of five rounds of the modified SELEX procedure performed on the zinc finger ZfQQR and a library of sequences containing 9 nucleotide degenerate region.

| Number | Sequence of library |
|--------|---------------------|
| 39 | GGGGTCCGA |
| 40 | GAGAGAGCG |
| 41 | TGGCAGCTT |
| 42 | CGAGATGGA |

On this basis, the ZFQQR binding consensus sequence 5'-GGNCGGNGGG-3' (SEQ ID No: 38) (FIG. 15) was obtained using WebLogo (Crooks G E, Hon G, Chandonia J M, Brenner S E WebLogo: A sequence logo generator, Genome Research, 14:1188-1190, (2004), Schneider T D, Stephens R M. 1990. Sequence Logos: A New Way to Display Consensus Sequences. Nucleic Acids Res. 18:6097-6100).

Example 13

Binding of Zinc Finger ZfQQR to the SELEX Consensus Sequence

To confirm that the consensus sequence obtained after five rounds of SELEX is bound by the zinc finger, a constant $K_D$ was measured using the nitrocellulose filter binding method. The assay was performed with radioactively labeled substrates described in the literature (LDNA, LRNA) and a consensus sequence (CDNA, CRNA) see FIG. 16:

```
LDNA:  TCACTGGGGAAGAAGAATCCTC    (SEQ ID No: 29)
LRNA:  GAGGAUUCUUCUUCCCCAGUGA    (SEQ ID No: 30)
CDNA:  TCACTGGTCGGTGGGAATCCTC    (SEQ ID No: 31)
CRNA:  GAGGAUUCCCACCGACCAGUGA    (SEQ ID No: 32)
```

Binding reaction contained 2 nM of labeled substrate, 2 µg poly dI-dC as a nonspecific competitor, 25 mM Tris pH 8.0, 100 mM KCl, 20 µM ZnSO₄, 2 mM DTT. The binding reaction was incubated for 30 min at room temperature and then filtered immediately through a nitrocellulose filter and washed with 8 volumes of reaction buffer of 25 mM Tris pH 8.0, 100 mM KCl, 20 µM ZnSO₄, 2 mM DTT. Measurement of the intensity of the signal coming from the retention of radioactively labeled substrate was made on an audioradiogram of the nitrocellulose filter using a Typhoon Trio scanner and ImageQuant TL software. $K_D$ binding constants were measured and for both substrates were similar, 188±38 nM for the binding of substrate described in the literature and 155±32 nM for the SELEX consensus sequence (FIG. 17).
The List of Sequences Identified in the Description:
SEQ ID No:1—DNA sequence of the gene rnhA ribonuclease HI (Gene ID 893801, BH0863) from *B. halodurans* (full length);
SEQ ID No:2—nucleotide sequence of zinc finger ZfQQR;
SEQ ID No:3—nucleotide sequence of the gene encoding the enzyme fusion containing a fragment of ribonuclease HI from *B. halodurans* with substitutions K81A, K89E and K123A with zinc finger ZfQQR—named catAEA-ZfQQR;
SEQ ID No:4—amino acid sequence of fusion containing a fragment of ribonuclease HI from *B. halodurans* with substitutions K81A, K89E, K123A and with zinc finger ZfQQR—named catAEA-ZfQQR;
SEQ ID No:5—nucleotide sequence of the gene encoding GQ variant of catAEA-ZfQQR (the enzyme fusion containing a fragment of ribonuclease HI from *B. halodurans* with substitutions introducing changes in the amino acid sequence of protein in positions K81A, K89E and K123A with zinc finger ZfQQR interdomain linker shortened by a fragment encoding amino acids in positions 138-148)—named GQ;
SEQ ID No:6—amino acid sequence of the GQ variant of catAEA-ZfQQR the enzyme fusion—named GQ;
SEQ ID No:7—nucleotide sequence of the GGKKQ variant of catAEA-ZfQQR (enzyme fusion containing a fragment of ribonuclease HI from *B. halodurans* with substitutions introducing changes in the amino acid sequence of protein in positions K81A, K89E and K123A with zinc finger ZfQQR with the interdomain linker by a fragment encoding amino acids in positions 138-139 and 141-146)—named GGKKQ;
SEQ ID No:8—amino acid sequence of GGKKQ variant of the enzyme fusion-named GGKKQ;
SEQ ID No:9—RNA strand of the substrate that contains the binding sequence for ZfQQR;
SEQ ID No:10—DNA strand of the substrate that contains the binding sequence for ZfQQR;
SEQ ID No:11—nucleotide sequence of Bhcatf primer;
SEQ ID No:12—nucleotide sequence of Bhcatr primer;
SEQ ID No:13—nucleotide sequence of BhZf primer;
SEQ ID No:14—nucleotide sequence of Kmf primer;
SEQ ID No:15—nucleotide sequence of Kmr primer;
SEQ ID No:16—nucleotide sequence of K81 Ar primer;
SEQ ID No:17—nucleotide sequence of K81Af primer;
SEQ ID No:18—nucleotide sequence of K89Er primer;
SEQ ID No:19—nucleotide sequence of K89Ef primer;
SEQ ID No:20—nucleotide sequence of K123Ar primer;
SEQ ID No:21—nucleotide sequence of K123Af primer;
SEQ ID No:22—nucleotide sequence of del11f primer;
SEQ ID No:23—nucleotide sequence of del11r primer;
SEQ ID No:24—nucleotide sequence of del5f primer;
SEQ ID No:25—nucleotide sequence of del5r primer;
SEQ ID No:26—sequence of the DNA strand of the substrate used for control of the SELEX method that contains the binding site for ZfQQR (Template A);
SEQ ID No:27—sequence of the DNA strand of the substrate used for control of the SELEX method that does not have a binding site for ZfQQR, instead a XhoI restriction site (Template B);
SEQ ID No:28—sequence of the DNA strand of the substrate used for construction of the library of DNA-RNA hybrids containing a central nonanucleotide random sequence (Template 9N);
SEQ ID No:29—nucleotide sequence of the DNA strand of the DNA-RNA hybrid that contains the ZfQQR binding sequence used for determining $K_D$;
SEQ ID No:30—nucleotide sequence of the RNA strand of the DNA-RNA hybrid that contains the ZfQQR binding sequence used for determining $K_D$;
SEQ ID No:31—nucleotide sequence of the DNA strand of the DNA-RNA hybrid that contains the consensus sequence inferred from SELEX used for determining $K_D$;

SEQ ID No:32—nucleotide sequence of the RNA strand of the DNA-RNA hybrid that contains the consensus sequence inferred from SELEX used for determining $K_D$;

SEQ ID No:33—primer 1—primer used for amplification of DNA of template A, B and 9N in the PCR reaction;

SEQ ID No:34—primer 2—primer used for amplification of DNA of template A, B and 9N in the PCR reaction;

SEQ ID No:35—primer ZFf—primer used in PCR for preparation of DNA construct of the fusion gene encoding the GST domain and the gene encoding the zinc finger Zf-QQ;

SEQ ID No:36—primer ZFr—primer used for preparation of DNA construct of the fusion gene encoding the GST domain and the gene encoding the zinc finger Zf-Q;

SEQ ID No:37—is nucleotide sequence of the gene encoding the fusion of the GST domain and the gene encoding the zinc finger ZfQQR (fusion GST-ZfQQR);

SEQ ID No: 38—the ZFQQR binding consensus sequence;

SEQ ID No: 39—the RNA strand of DNA-RNA hybrid containing the binding site for zinc finger ZFQQR;

SEQ ID No: 40—the DNA strand of the DNA-RNA hybrid containing the binding site for zinc finger ZFQQR.

The invention is further described by the following numbered paragraphs:

1. A ribonuclease, which cleaves RNA strand in DNA-RNA hybrids, wherein ribonuclease is a fusion protein comprising
    catalytic domain of ribonuclease HI (RNase HI) or derivative thereof, and wherein catalytic domain of ribonuclease HI or derivative thereof does not bind the substrate but retains the catalytic activity,
    preferably wherein catalytic domain of RNase HI or derivative thereof does not comprises RNase HI hybrid binding domain,
    and wherein catalytic domain of RNase HI or derivative thereof comprises change(s) in the substrate binding region, preferably selected from substitutions, deletions or insertions of at least one amino acid which change(s) provides destabilization of binding substrate by such catalytic domain of RNase HI or derivative thereof,
    with a zinc finger DNA-RNA hybrid binding domain, wherein the zinc finger binding domain has the ability to bind to specific sequence in the DNA-RNA hybrid.

2. The ribonuclease according to paragraph 1, wherein the zinc finger domain is a derivative of the zinc finger ZfQQR, preferably a polypeptide encoded by nucleotides from 19 to 303 of the sequence ZfQQR shown in SEQ ID No.2.

3. The ribonuclease according to paragraphs 1 or 2, wherein the catalytic domain of RNase HI is from *Bacillus halodurans*, preferably comprising polypeptide encoded by nucleotides 175 to 588 of the rnhA gene shown in SEQ ID No:1, and more preferably wherein the catalytic domain of RNase HI comprises at least one substitution of one amino acid residue in the substrate binding domain selected from: K81A, K89E and K123A, and preferably contains all substitutions K81A, K89E and K123A.

4. The ribonuclease according to paragraphs 1-3, wherein it comprises a fusion protein catAEA-ZfQQR as shown in SEQ ID No.4, or a fusion protein GQ as shown in SEQ ID No.6, or comprises a fusion protein GGKKQ as shown in SEQ ID No.8.

5. A composition comprising the ribonuclease according to paragraphs 1-4.

6. Use of ribonuclease according to paragraphs 1-4 or composition according to paragraph 5 for the cleavage of the RNA strand in DNA-RNA hybrids, preferably wherein the cleavage of the RNA strand in DNA-RNA hybrids is located 2-16 nucleotides, preferably 5-7 nucleotides, away from the binding site for the zinc finger.

7. A method of obtaining an engineered variant of RNase HI that cleaves RNA strand in DNA-RNA hybrids comprising the following steps:
    a) obtaining the RNase HI catalytic domain that does not bind the substrate but retains the catalytic activity preferably by the removal of hybrid binding domain and/or substitution of amino acids involved in substrate binding,
    and introducing change(s) in the substrate binding region of the catalytic domain of RNase HI, preferably selected from substitutions, deletions or insertions of at least one amino acid which change(s) provides destabilization of binding substrate by such catalytic domain of RNase,
    b) obtaining an engineered RNase HI by making a fusion protein comprising the RNase HI catalytic domain obtained in step a) with a binding domain that has the ability to bind to specific sequences in the DNA-RNA hybrid, preferably with a zinc finger DNA-RNA hybrid binding domain,
        preferably wherein the zinc finger domain is a derivative of the zinc finger ZfQQR, preferably a polypeptide encoded by nucleotides from 19 to 303 of the sequence ZfQQR shown in SEQ ID No.2,
        and preferably wherein the catalytic domain of RNase HI is from *B. halodurans*, preferably comprising a polypeptide encoded by nucleotides 175 to 588 of the rnhA gene shown in SEQ ID No:1.

8. A method of determining the sequence preference of DNA-RNA hybrid binding protein(s) or its domain(s), wherein the method comprises the following steps:
    a) contacting of the purified protein or its domain, with a mixture of a library of DNA-RNA hybrids substrates, wherein DNA-RNA hybrid substrates comprise randomized sequences in the central part, preferably randomized in 9 or 10 nucleotide positions, with flanking sequences fixed and allowing a tested protein or its domain to bind the sequence to which it has an affinity;
    b) separating unbound DNA-RNA hybrids by immobilization of protein or its domain, with bound DNA-RNA hybrid, to the resin, preferably glutathione agarose;
    c) removing the unbound hybrids;
    d) isolating the recombinant protein, together with the associated DNA-RNA hybrids, preferably by adding a buffer containing glutathione;
    e) amplification of the isolated hybrid using PCR, preferably RT-PCR, wherein in the amplification reaction the primers complementary to invariant sequences flanking the randomized region are used, and wherein during the PCR reaction on one of the primer the sequence of RNA polymerase promoter is added in order to obtain double-stranded DNA for in vitro transcription with RNA polymerase;
    f) reverse transcription is performed using reverse transcriptase that does not possess the RNase H activity and a DNA primer complementary to the 3' end of the RNA template in order to obtain a DNA-RNA hybrid, and steps a) to f) are preferably repeated.

9. The method of paragraph 8, wherein the promoter sequence comprises the promoter sequence for T7 RNA polymerase and RNA polymerase is T7 RNA polymerase.

10. The method according to paragraph 8 or 9, wherein the protein or its domain is a recombinant protein or a recombinant domain, preferably comprising zinc finger(s), and preferably wherein the protein or its domain is the fusion of RNase HI or a derivative, preferably RNase HI is from *B. halodurans*, preferably comprising polypeptide encoded by nucleotides 175 to 588 of rnhA gene shown in SEQ ID No:1 and a zinc finger.

11. The method according to paragraph 8-10, wherein the protein or its domain is the fusion of the zinc finger domain and the glutathione S-transferase domain (GST), preferably the fusion of the zinc finger domain and GST encoded by SEQ ID No:37.

12. The method according to paragraphs 8-10, wherein the zinc finger has the ability to bind to a specific sequence in the DNA-RNA hybrid.

13. The method according to paragraphs 8-12 wherein the zinc finger is ZfQQR, preferably of sequence encoded by nucleotides from 19 to 303 of the sequence ZfQQR shown in SEQ ID No.2.

14. The method of obtaining a library of DNA-RNA hybrids comprising the flowing steps:
a) PCR amplification of the library of DNA oligonucleotides containing a degenerate sequence in the central position, flanked by invariant sequences, which include a promoter sequence for RNA polymerase,
b) synthesis of RNA strand using an RNA polymerase on the double stranded DNA obtained in a) used as a template,
c) reverse transcription of the primer complementary to the invariant sequence present at the 3' end of RNA obtained in b) with a reverse transcriptase that does not possess the ribonuclease H activity, wherein during the reverse transcription the RNA strand is not degraded, and the hybrid nucleic acid molecule consisting of complementary RNA and DNA strands is obtained,
preferably wherein oligonucleotides contain a degenerate sequence in the central position comprising randomized 9 or 10 nucleotide positions,
and preferably wherein the promoter sequence comprises the promoter sequence for T7 RNA polymerase and RNA polymerase is the T7 RNA polymerase.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A ribonuclease variant, which cleaves RNA strand in DNA-RNA hybrids, wherein the ribonuclease is a fusion protein comprising:
   (a) a derivative of a catalytic domain of ribonuclease HI (RNase HI), wherein
      (i) the derivative of the catalytic domain of RNase HI does not bind the substrate but retains the catalytic activity,
      (ii) the derivative of the catalytic domain of RNase HI does not comprise a RNase HI binding domain which binds said DNA-RNA hybrids,
      (iii) the derivative of the catalytic domain of RNase HI comprises a polypeptide encoded by a nucleotide sequence consisting of nucleotides 175 to 588 that is the rnhA gene shown in SEQ ID NO: 1, and
      (iv) the derivative of the catalytic domain of RNase HI comprises at least one substitution of one amino acid residue in the substrate binding domain of said RNase HI selected from: K81A, K89E and K123A, and
   (b) a zinc finger DNA-RNA hybrid binding domain, wherein the zinc finger binding domain has the ability to bind to specific sequence in the DNA-RNA hybrid.

2. The ribonuclease variant according to claim 1, wherein the zinc finger DNA-RNA hybrid binding domain is a derivative of the zinc finger ZfQQR.

3. The ribonuclease variant according to claim 1 comprises a fusion protein catAEA-ZfQQR consisting of SEQ ID NO:4, a fusion protein GQ consisting of SEQ ID NO:6, or a fusion protein GGKKQ consisting of SEQ ID NO:8.

4. A composition comprising the ribonuclease variant according to claim 1.

5. The ribonuclease variant according to claim 1, wherein the catalytic domain comprises all substitutions K81A, K89E and K123A.

6. The ribonuclease variant according to claim 2, wherein the derivative of the zinc finger ZfQQR is encoded by nucleotides from 19 to 303 of the nucleotide sequence of ZfQQR consisting of SEQ ID NO:2.

7. A method of obtaining producing the ribonuclease variant of claim 1 comprising the following steps: a) obtaining the RNase HI catalytic domain that does not bind the substrate but retains the catalytic activity preferably by the removal of hybrid binding domain and/or substitution of amino acids involved in substrate binding, and introducing change(s) in the substrate binding region of the catalytic domain of RNase HI selected from substitutions, deletions or insertions of at least one amino acid which change(s) provides destabilization of binding substrate by such catalytic domain of RNase, b) obtaining an RNase HI by making a fusion protein comprising the RNase HI catalytic domain obtained in step a) with a binding domain that has the ability to bind to specific sequences in the DNA-RNA hybrid with a zinc finger DNA-RNA hybrid binding domain, wherein the zinc finger domain is a derivative of the zinc finger ZfQQR, a polypeptide encoded by nucleotides from 19 to 303 of the sequence ZfQQR shown in SEQ ID No:2, and wherein the catalytic domain of RNase HI comprises a polypeptide encoded by nucleotides 175 to 588 of the rnhA gene shown in SEQ ID NO:1, thereby producing said ribonuclease variant.

* * * * *

SEQUENCE LISTING

```
<160> NUMBER OF SEQ ID NOS: 40

<210> SEQ ID NO 1
<211> LENGTH: 688
<212> TYPE: DNA
<213> ORGANISM: Bacillus halodurans

<400> SEQUENCE: 1
atggcaaagt caaaatacta tgtcgtatgg aatggacgga agcccggcat ttatacgagc      60
tggtctgcat gtgaagctca agtaaaagga tataccggcg ccaaatttaa atcctatcct     120
tccaaggaag aagcagaggc tgcttttaga ggagaagagg caacaccgaa gcttgcaaaa     180
gaggagatta tttgggagag cctgtctgta gatgttggca gccaagggaa tcccggaatt     240 gtgaatata aaggcgttga tacgaaaacg ggagaagtcc tttttgaacg agagccgatt      300
ccgatcggga caaacaatat gggtgagttt ctcgcgatcg ttcacgggct tcgttacctt     360
aaggaacgga acagtcgtaa gccgatctat tctgattccc agacggcaat caaatgggtg     420
aaggataaaa aagcaaaatc gaccctcgtg cgcaatgaag aaacagcgct tatttggaag     480
cttgtagatg aagcggagga gtggctaaac actcatacct atgaaacgcc catcttaaaa     540
tggcagaccg ataagtgggg ggaaattaag gccgattacg ggagaaaagg taccgacgac     600
gacgacaagg ccatggcgat atcggatccg aattcgagct ccgtcgacaa gcttgcggcc     660
gcactcgagc accaccacca ccaccact                                        688

<210> SEQ ID NO 2
<211> LENGTH: 305
<212> TYPE: DNA
<213> ORGANISM: Artificial Sequence
<220> FEATURE:
<223> OTHER INFORMATION: Description of Artificial Sequence: Synthetic
      ZfQQR nucleotide sequence

<400> SEQUENCE: 2
ccatggaaaa actgcgtaac ggttctggtg acccgggtaa aaaaaaacag cacgcgtgcc      60
cggaatgcgg taaatctttc tctcagtctt ctaacctgca gaaacaccag cgtacccaca     120
ccggtgaaaa accgtacaaa tgtccagaat gtggcaaaag ctttagtcaa agttctaatc     180
```

-continued

```
ttcaaaaaca tcaacgcacg cataccggcg agaagccata taagtgtccg gagtgcggca      240
aaagcttctc ccgctctgat cacctccagc gtcatcagcg cactcatcag aacaaaaaac      300
tcgag                                                                 305
```

<210> SEQ ID NO 3
<211> LENGTH: 720
<212> TYPE: DNA
<213> ORGANISM: Artificial Sequence
<220> FEATURE:
<223> OTHER INFORMATION: Description of Artificial Sequence: Synthetic
      fusion catAEA-ZfQQR - nucleotide sequence

<400> SEQUENCE: 3

```
atggcaaaag aggagattat ttgggagagc ctgtctgtag atgttggcag ccaagggaat       60
cccggaattg tggaatataa aggcgttgat acgaaaacgg gagaagtcct ttttgaacga      120
gagccgattc cgatcgggac aaacaatatg ggtgagtttc tcgcgatcgt tcacgggctt      180
cgttacctta aggaacggaa cagtcgtaag ccgatctatt ctgattccca gacggcaatc      240
gcatgggtga aggataaaaa agcagaatcg accctcgtgc gcaatgaaga aacagcgctt      300
atttggaagc ttgtagatga agcggaggag tggctaaaca ctcataccta tgaaacgccc      360
atcttagcat ggcagaccga taagtggggg gaaattaagg ccgattacgg agaaaaggt      420 tctggtgacc cgggtaaaaa aaacagcac gcgtgcccgg aatgcggtaa atctttctct      480
cagtcttcta acctgcagaa acaccagcgt acccacaccg gtgaaaaacc gtacaaatgt      540
ccagaatgtg gcaaaagctt tagtcaaagt tctaatcttc aaaaacatca acgcacgcat      600
accggcgaga agccatataa gtgtccggag tgcggcaaaa gcttctcccg ctctgatcac      660
ctccagcgtc atcagcgcac tcatcagaac aaaaaactcg agcaccacca ccaccaccac      720
```

<210> SEQ ID NO 4
<211> LENGTH: 240
<212> TYPE: PRT
<213> ORGANISM: Artificial Sequence
<220> FEATURE:
<223> OTHER INFORMATION: Description of Artificial Sequence: Synthetic
      amino acid sequence of fusion catAEA-ZfQQR

<400> SEQUENCE: 4

```
Met Ala Lys Glu Glu Ile Ile Trp Glu Ser Leu Ser Val Asp Val Gly
1               5                   10                  15

Ser Gln Gly Asn Pro Gly Ile Val Glu Tyr Lys Gly Val Asp Thr Lys
            20                  25                  30

Thr Gly Glu Val Leu Phe Glu Arg Glu Pro Ile Pro Ile Gly Thr Asn
        35                  40                  45

Asn Met Gly Glu Phe Leu Ala Ile Val His Gly Leu Arg Tyr Leu Lys
    50                  55                  60

Glu Arg Asn Ser Arg Lys Pro Ile Tyr Ser Asp Ser Gln Thr Ala Ile
65                  70                  75                  80

Ala Trp Val Lys Asp Lys Lys Ala Glu Ser Thr Leu Val Arg Asn Glu
                85                  90                  95

Glu Thr Ala Leu Ile Trp Lys Leu Val Asp Glu Ala Glu Glu Trp Leu
            100                 105                 110

Asn Thr His Thr Tyr Glu Thr Pro Ile Leu Ala Trp Gln Thr Asp Lys
        115                 120                 125

Trp Gly Glu Ile Lys Ala Asp Tyr Gly Arg Lys Gly Ser Gly Asp Pro
    130                 135                 140
```

Gly Lys Lys Lys Gln His Ala Cys Pro Glu Cys Gly Lys Ser Phe Ser
145                 150                 155                 160

Gln Ser Ser Asn Leu Gln Lys His Gln Arg Thr His Thr Gly Glu Lys
            165                 170                 175

Pro Tyr Lys Cys Pro Glu Cys Gly Lys Ser Phe Ser Gln Ser Ser Asn
        180                 185                 190

Leu Gln Lys His Gln Arg Thr His Thr Gly Glu Lys Pro Tyr Lys Cys
    195                 200                 205

Pro Glu Cys Gly Lys Ser Phe Ser Arg Ser Asp His Leu Gln Arg His
    210                 215                 220

Gln Arg Thr His Gln Asn Lys Lys Leu Glu His His His His His His
225                 230                 235                 240

<210> SEQ ID NO 5
<211> LENGTH: 687
<212> TYPE: DNA
<213> ORGANISM: Artificial Sequence
<220> FEATURE:
<223> OTHER INFORMATION: Description of Artificial Sequence: Synthetic
      fusion of variant GQ of catAEA-ZfQQR nucleotide
      sequence

<400> SEQUENCE: 5
atggcaaaag aggagattat ttgggagagc ctgtctgtag atgttggcag ccaagggaat      60
cccggaattg tgaatataa aggcgttgat acgaaaacgg gagaagtcct ttttgaacga     120
gagccgattc cgatcgggac aaacaatatg ggtgagtttc tcgcgatcgt tcacgggctt     180 cgttaccta aggaacggaa cagtcgtaag ccgatctatt ctgattccca gacggcaatc     240
gcatgggtga aggataaaaa agcagcatcg accctcgtgc gcaatgaaga aacagcgctt     300
atttggaagc ttgtagatga agcggaggag tggctaaaca ctcataccta tgaaacgccc     360
atcttagcat ggcagaccga taagtgggg gaaattaagg ccgattacgg gcagcacgcg     420
tgcccggaat gcggtaaatc tttctctcag tcttctaacc tgcagaaaca ccagcgtacc     480
cacaccggtg aaaaaccgta caatgtcca gaatgtggca aagctttag tcaaagttct     540 aatcttcaaa aacatcaacg cacgcatacc ggcgagaagc catataagtg tccggagtgc     600
ggcaaaagct ctccccgctc tgatcacctc agcgtcatc agcgcactca tcagaacaaa     660
aaactcgagc accaccacca ccaccac                                        687

<210> SEQ ID NO 6
<211> LENGTH: 229
<212> TYPE: PRT
<213> ORGANISM: Artificial Sequence
<220> FEATURE:
<223> OTHER INFORMATION: Description of Artificial Sequence: Synthetic
      fusion of variant GQ of catAEA-ZfQQR amino acid
      sequence

<400> SEQUENCE: 6

Met Ala Lys Glu Glu Ile Ile Trp Glu Ser Leu Ser Val Asp Val Gly
1               5                   10                  15

Ser Gln Gly Asn Pro Gly Ile Val Glu Tyr Lys Gly Val Asp Thr Lys
            20                  25                  30

Thr Gly Glu Val Leu Phe Glu Arg Glu Pro Ile Pro Ile Gly Thr Asn
        35                  40                  45

Asn Met Gly Glu Phe Leu Ala Ile Val His Gly Leu Arg Tyr Leu Lys
    50                  55                  60

```
Glu Arg Asn Ser Arg Lys Pro Ile Tyr Ser Asp Ser Gln Thr Ala Ile
 65                  70                  75                  80

Ala Trp Val Lys Asp Lys Lys Ala Ala Ser Thr Leu Val Arg Asn Glu
                 85                  90                  95

Glu Thr Ala Leu Ile Trp Lys Leu Val Asp Glu Ala Glu Glu Trp Leu
            100                 105                 110

Asn Thr His Thr Tyr Glu Thr Pro Ile Leu Ala Trp Gln Thr Asp Lys
        115                 120                 125

Trp Gly Glu Ile Lys Ala Asp Tyr Gly Gln His Ala Cys Pro Glu Cys
    130                 135                 140

Gly Lys Ser Phe Ser Gln Ser Ser Asn Leu Gln Lys His Gln Arg Thr
145                 150                 155                 160

His Thr Gly Glu Lys Pro Tyr Lys Cys Pro Glu Cys Gly Lys Ser Phe
                165                 170                 175

Ser Gln Ser Ser Asn Leu Gln Lys His Gln Arg Thr His Thr Gly Glu
            180                 185                 190

Lys Pro Tyr Lys Cys Pro Glu Cys Gly Lys Ser Phe Ser Arg Ser Asp
        195                 200                 205

His Leu Gln Arg His Gln Arg Thr His Gln Asn Lys Lys Leu Glu His
    210                 215                 220

His His His His His
225
```

<210> SEQ ID NO 7
<211> LENGTH: 696
<212> TYPE: DNA
<213> ORGANISM: Artificial Sequence
<220> FEATURE:
<223> OTHER INFORMATION: Description of Artificial Sequence: Synthetic
      fusion of variant  GGKKQ of catAEA-ZfQQR nucleotide
      sequence

<400> SEQUENCE: 7

```
atggcaaaag aggagattat ttgggagagc ctgtctgtag atgttggcag ccaagggaat    60
cccggaattg tggaatataa aggcgttgat acgaaaacgg gagaagtcct ttttgaacga   120
gagccgattc cgatcgggac aaacaatatg ggtgagtttc tcgcgatcgt tcacgggctt   180
cgttacctta aggaacggaa cagtcgtaag ccgatctatt ctgattccca gacggcaatc   240
gcatgggtga aggataaaaa agcagcatcg accctcgtgc gcaatgaaga aacagcgctt   300
atttggaagc ttgtagatga agcggaggag tggctaaaca ctcataccta tgaaacgccc   360
atcttagcat ggcagaccga taagtggggg gaaattaagg ccgattacgg gggcaaaaaa   420
cagcacgcgt gcccggaatg cggtaaatct ttctctcagt cttctaacct gcagaaacac   480
cagcgtaccc acaccggtga aaaccgtac aaatgtccag aatgtggcaa agctttagt    540
caaagttcta atcttcaaaa acatcaacgc acgcataccg gcgagaagcc atataagtgt   600
ccggagtgcg gcaaaagctt ctcccgctct gatcacctcc agcgtcatca gcgcactcat   660
cagaacaaaa aactcgagca ccaccaccac caccac                             696
```

<210> SEQ ID NO 8
<211> LENGTH: 232
<212> TYPE: PRT
<213> ORGANISM: Artificial Sequence
<220> FEATURE:
<223> OTHER INFORMATION: Description of Artificial Sequence: Synthetic
      fusion of variant  GGKKQ of catAEA-ZfQQR amino acid
      sequence

<400> SEQUENCE: 8

Met Ala Lys Glu Glu Ile Ile Trp Glu Ser Leu Ser Val Asp Val Gly
1               5                   10                  15

Ser Gln Gly Asn Pro Gly Ile Val Tyr Lys Gly Val Asp Thr Lys
            20                  25                  30

Thr Gly Glu Val Leu Phe Arg Glu Pro Ile Pro Ile Gly Thr Asn
        35                  40                  45

Asn Met Gly Glu Phe Leu Ala Ile Val His Gly Leu Arg Tyr Leu Lys
    50                  55                  60

Glu Arg Asn Ser Arg Lys Pro Ile Tyr Ser Asp Ser Gln Thr Ala Ile
65                  70                  75                  80

Ala Trp Val Lys Asp Lys Lys Ala Ala Ser Thr Leu Val Arg Asn Glu
                85                  90                  95

Glu Thr Ala Leu Ile Trp Lys Leu Val Asp Glu Ala Glu Glu Trp Leu
            100                 105                 110

Asn Thr His Thr Tyr Glu Thr Pro Ile Leu Ala Trp Gln Thr Asp Lys
        115                 120                 125

Trp Gly Glu Ile Lys Ala Asp Tyr Gly Gly Lys Lys Gln His Ala Cys
    130                 135                 140

Pro Glu Cys Gly Lys Ser Phe Ser Gln Ser Ser Asn Leu Gln Lys His
145                 150                 155                 160

Gln Arg Thr His Thr Gly Glu Lys Pro Tyr Lys Cys Pro Glu Cys Gly
                165                 170                 175

Lys Ser Phe Ser Gln Ser Ser Asn Leu Gln Lys His Gln Arg Thr His
            180                 185                 190

Thr Gly Glu Lys Pro Tyr Lys Cys Pro Glu Cys Gly Lys Ser Phe Ser
        195                 200                 205

Arg Ser Asp His Leu Gln Arg His Gln Arg Thr His Gln Asn Lys Lys
    210                 215                 220

Leu Glu His His His His His His
225                 230

<210> SEQ ID NO 9
<211> LENGTH: 75
<212> TYPE: RNA
<213> ORGANISM: Artificial Sequence
<220> FEATURE:
<223> OTHER INFORMATION: Description of Artificial Sequence: Synthetic
      RNA sequence that contains the binding sequence for
      ZfQQR

<400> SEQUENCE: 9
agaacuagug gaucaaccgg gcugcaggaa uucgauauca agcuuaucga uaccguggcg      60
guucuucccc aagcc                                                       75

<210> SEQ ID NO 10
<211> LENGTH: 74
<212> TYPE: DNA
<213> ORGANISM: Artificial Sequence
<220> FEATURE:
<223> OTHER INFORMATION: Description of Artificial Sequence: Synthetic
      DNA sequence of the substrate that contains the binding
      sequence for ZfQQR

<400> SEQUENCE: 10
gcttggggaa gaaccgccac ggtatcgata agcttgatat cgaattcctg cagcccggtt      60
gatccactag ttct                                                        74

```
<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gacgcatatg gcaaaagagg agattatttg gg                                32

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtggtacctt ttctcccgta atcggc                                       26

<210> SEQ ID NO 13
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggttctggtg acccggg                                                 17

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggatcgcag tggtgagtaa c                                            21

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgggaaaaca gcattccagg tattag                                       26

<210> SEQ ID NO 16
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccgtctggga atcagaatag atc                                          23
```

```
<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
caatcgcatg ggtgaaggat aaaaaag                                          27

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ctgctttttt atccttcacc c                                                21

<210> SEQ ID NO 19
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
caatcgcatg ggtgaaggat aaaaaag                                          27

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
taagatgggc gtttcatagg tatg                                             24

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcatggcaga ccgataagtg                                                  20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggctccggcc agcacgcgtg cccgg                                            25

<210> SEQ ID NO 23
```

```
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agaaccgctc ccgtaatcgg ccttaatttc c                                    31

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caaaaaacag cacgcgtgcc c                                               21

<210> SEQ ID NO 25
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cccccgtaat cggccttaat ttccc                                           25

<210> SEQ ID NO 26
<211> LENGTH: 78
<212> TYPE: DNA
<213> ORGANISM: Artificial Sequence
<220> FEATURE:
<223> OTHER INFORMATION: Description of Artificial Sequence: Synthetic
      DNA sequence that contains the binding site for ZfQQR

<400> SEQUENCE: 26
gagatctaga cggaacatga aggggaagaa ttctatgctt agtgagatct agagccctat     60
agtgagtcgt attaaatt                                                   78

<210> SEQ ID NO 27
<211> LENGTH: 78
<212> TYPE: DNA
<213> ORGANISM: Artificial Sequence
<220> FEATURE:
<223> OTHER INFORMATION: Description of Artificial Sequence: Synthetic
      DNA sequence that does not contain a binding site for
      ZfQQR

<400> SEQUENCE: 27
gagatctaga cggaacatga agctcgagcc ttctatgctt agtgagatct agagccctat     60
agtgagtcgt attaaatt                                                   78

<210> SEQ ID NO 28
<211> LENGTH: 78
<212> TYPE: DNA
<213> ORGANISM: Artificial Sequence
<220> FEATURE:
<223> OTHER INFORMATION: Description of Artificial Sequence: Synthetic
      template sequence with nonanucleotide random sequence
<220> FEATURE:
<221> NAME/KEY: modified_base
<222> LOCATION: (22)..(30)
```

<223> OTHER INFORMATION: a, c, t, g, unknown or other

<400> SEQUENCE: 28
gagatctaga cggaacatgt annnnnnnnn tactatgctt agtgagatct agagccctat    60
agtgagtcgt attaaatt                                                 78

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA sequence of the DNA-RNA hybrid

<400> SEQUENCE: 29
tcactgggga agaagaatcc tc                                            22

<210> SEQ ID NO 30
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA sequence of the DNA-RNA hybrid

<400> SEQUENCE: 30
gaggauucuu cuuccccagu ga                                            22

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA sequence of the DNA-RNA hybrid

<400> SEQUENCE: 31
tcactggtcg gtgggaatcc tc                                            22

<210> SEQ ID NO 32
<211> LENGTH: 22
<212> TYPE: RNA
<213> ORGANISM: Artificial Sequence
<220> FEATURE:
<223> OTHER INFORMATION: Description of Artificial Sequence: Synthetic
      RNA sequence of the DNA-RNA hybrid

<400> SEQUENCE: 32
gaggauuccc accgaccagu ga                                            22

<210> SEQ ID NO 33
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aatttaatac gactcactat agggctctag atctcactaa gcatag                  46

<210> SEQ ID NO 34
<211> LENGTH: 19
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 34
gagatctaga cggaacatg                                                19

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggttctggtg acccggg                                                  17

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgggaaaaca gcattccagg tattag                                        26

<210> SEQ ID NO 37
<211> LENGTH: 975
<212> TYPE: DNA
<213> ORGANISM: Artificial Sequence
<220> FEATURE:
<223> OTHER INFORMATION: Description of Artificial Sequence: Synthetic
      fusion sequence of the GST domain and zinc finger
      ZfQQR

<400> SEQUENCE: 37
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acgtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg atgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat   660
ctggttccgc gtggatcccc ggaattcccg ggtaaaaaaa acagcacgc gtgcccggaa    720 tgcggtaaat ctttctctca gtcttctaac ctgcagaaac accagcgtac ccacaccggt   780
gaaaaaccgt acaatgtcc agaatgtggc aaaagcttta gtcaaagttc taatcttcaa    840 aacatcaac gcacgcatac cggcgagaag ccatataagt gtccggagtg cggcaaaagc    900
ttctcccgct ctgatcacct ccagcgtcat cagcgcactc atcagaacaa aaaactcgag   960
cggccgcatc gtgac                                                   975
```

```
<210> SEQ ID NO 38
<211> LENGTH: 10
<212> TYPE: DNA
<213> ORGANISM: Artificial Sequence
<220> FEATURE:
<223> OTHER INFORMATION: Description of Artificial Sequence: Synthetic
      ZFQQR binding consensus sequence
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (7)..(7)
<223> OTHER INFORMATION: a, c, t, g, unknown or other

<400> SEQUENCE: 38 ggncggnggg                                                              10

<210> SEQ ID NO 39
<211> LENGTH: 75
<212> TYPE: RNA
<213> ORGANISM: Artificial Sequence
<220> FEATURE:
<223> OTHER INFORMATION: Description of Artificial Sequence: Synthetic
      RNA sequence of DNA-RNA hybrid containing the binding
      site for zinc finger ZfQQR

<400> SEQUENCE: 39
agaacuagug gaucaaccgg gcugcaggaa uucgauauca agcuuaucga uaccguggcg        60
guucuucccc aagcc                                                        75

<210> SEQ ID NO 40
<211> LENGTH: 75
<212> TYPE: DNA
<213> ORGANISM: Artificial Sequence
<220> FEATURE:
<223> OTHER INFORMATION: Description of Artificial Sequence: Synthetic
      DNA sequence of DNA-RNA hybrid containing the binding
      site for zinc finger ZfQQR

<400> SEQUENCE: 40
ggcttgggga agaaccgcca cggtatcgat aagcttgata tcgaattcct gcagcccggt       60
tgatccacta gttct                                                        75
```